United States Patent [19]

Foulon et al.

[11] Patent Number: 5,696,145
[45] Date of Patent: Dec. 9, 1997

[54] 1-BENZYL-1,3-DIHYDROINDOL-2-ONE DERIVATIVES, THEIR PREPARATION AND THE PHARMACEUTICAL COMPOSITIONS IN WHICH THEY ARE PRESENT

[75] Inventors: Loïc Foulon, Pinsaguel; Georges Garcia, St Gely Du Fesc; Daniel Mettefeu, Grabels; Claudine Serradeil-Legal, Escalquens; Gérard Valette, La Croix-Sasgarde, all of France

[73] Assignee: Sanofi, Paris, France

[21] Appl. No.: 482,081

[22] Filed: Jun. 7, 1995

Related U.S. Application Data

[62] Division of Ser. No. 282,644, Jul. 29, 1994, Pat. No. 5,618,833.

[30] Foreign Application Priority Data

Jul. 30, 1993 [FR] France .................. 93 09405

[51] Int. Cl.[6] .............. C07D 491/20; C07D 471/10; C07D 209/34; A61K 31/40
[52] U.S. Cl. .............. 514/409; 548/411; 548/410; 546/15; 544/70; 544/6; 544/230; 514/235.2; 540/543
[58] Field of Search .............. 548/411, 410; 514/409, 278, 235.2; 546/15; 544/70

[56] References Cited

U.S. PATENT DOCUMENTS 4,226,860 10/1980 Demerson et al. .............. 424/240

*Primary Examiner*—Mukund J. Shah
*Assistant Examiner*—King Lit Wong
*Attorney, Agent, or Firm*—Bacon & Thomas

[57] ABSTRACT

The present invention relates to 1-benzyl-1,3-dihydroindol-2-one derivatives of the formula

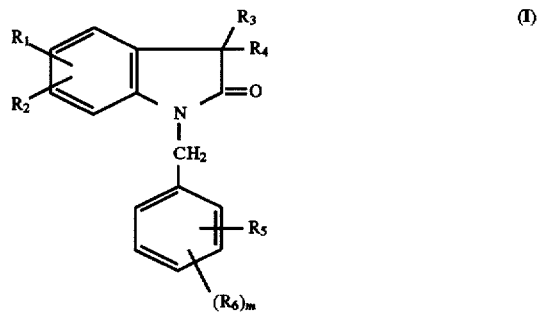

to their preparation and to the pharmaceutical compositions in which they are present. These derivatives have an affinity for the vasopressin and oxytocin receptors.

12 Claims, No Drawings

1-BENZYL-1,3-DIHYDROINDOL-2-ONE DERIVATIVES, THEIR PREPARATION AND THE PHARMACEUTICAL COMPOSITIONS IN WHICH THEY ARE PRESENT

This application is a division of application Ser. No. 08/282,644, filed Jul. 29, 1994, now U.S. Pat. No. 5,618,833.

The present invention relates to 1-benzyl-1,3-dihydroindol-2-one derivatives, to their preparation and to the pharmaceutical compositions in which they are present.

Several patents or patent applications describe 1-benzyl-1,3-dihydroindol-2-one derivatives.

Patent application JP-87/227987 describes the preparation of the oxothiolan derivative of the formula

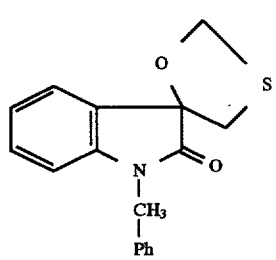

Patent applications EP 28906 and EP 66378 describe compounds of the formula

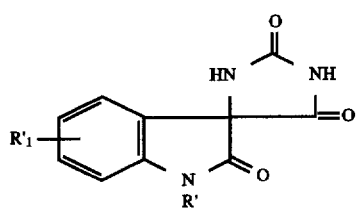

in which R' can be a $CH_2Ph$ group, more particularly 3,4-$Cl_2C_6H_3CH_2$. These compounds lower the sorbitol level in the sciatic nerve.

U.S. Pat. No. 4,226,860 describes compounds of the formula

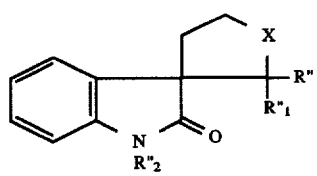

in which:

R" is an alkyl or a carboxyalkyl,
R"$_1$ is an alkyl,
R"$_2$ is an alkyl or phenylalkyl, and
X is a methylene or an oxygen.

These compounds are useful for the treatment of hypertension.

Patent DE 3529994 describes compounds of the formula

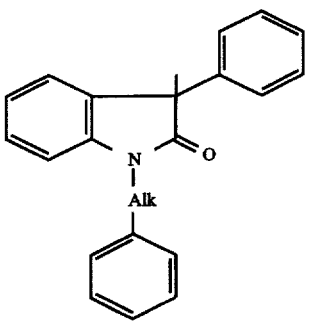

in which each of the 3 phenyl rings can carry a variety of substituents. These compounds are calcium antagonists.

Patent application EP 344634 describes indolone or quinolone derivatives of the formula

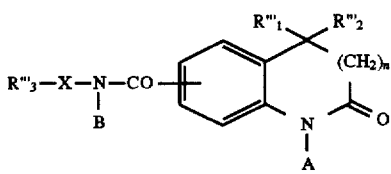

in which:

n=0 or 1,
A and B are hydrogen, an alkyl, an alkenyl, an alkynyl, a benzyl or a cycloalkyl, and
R'''$_1$ and R'''$_2$ independently are an alkyl, an alkenyl or a cycloalkyl, or R'''$_1$ and R'''$_2$ together are a $C_3$–$C_7$-cycloalkane.

These compounds are platelet aggregation inhibitors.

U.S. Pat. No. 4,806,651 describes the preparation of compounds of the formula

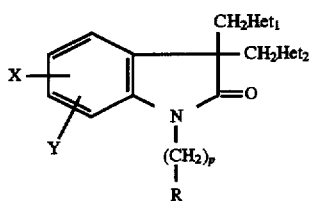

in which:

Het$_1$ and Het$_2$ are heterocycles,
R can be a substituted phenyl, and
p is zero or one.

These compounds are useful for the treatment of cognitive or neurological dysfunctions.

Several patent applications have recently described families of compounds of non-peptide structure which are active on the vasopressin and/or oxytocin receptors. The following may be mentioned: patent applications EP 382 185, EP 444 945 and EP 514 667, EP 469 984, EP 526 348 and EP 581 939, patent applications WO 91/05 549 and WO 93/15 051 and, more particularly, patent application JP-03/127732. The latter describes indole-3-propionic acid derivatives of the formula

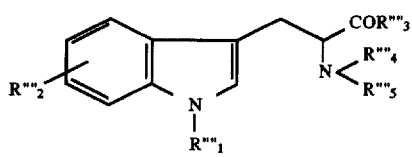

in which:

R''''$_1$ is hydrogen, an alkyl, an alkenyl, a phenylalkyl, a tetrahydrofuryl, an alkoxycarbonyl, an alkoxycarbonylalkyl, a carboxyalkyl or an alkanoyl;

R''''$_2$ is hydrogen, a hydroxyl, an alkoxy, an alkyl, a phenylalkyl, a phenylalkoxy or a halogen;

R''''$_3$ is a hydrogen, an alkoxy, a free or substituted amino group or an amino acid residue;

R''''$_4$ is hydrogen, an alkyl or a phenylalkyl; and

R''''$_5$ is a benzoyl, a phenyl, an alkyl, a phenylalkenylcarbonyl, a thienylcarbonyl, a phenylsulfonyl, a pyridylcarbonyl or an imidazolylcarbonyl, it being possible for the phenyl and alkyl groups of the substituent R''''$_5$ to be substituted.

These compounds are vasopressin antagonists.

U.S. Pat. No. 4,803,217 claims hapalindolinones obtained by fermentation, which are vasopressin antagonists. These compounds are represented by the following formula:

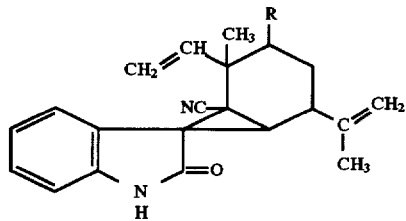

in which R is H or Cl.

The 1-benzyl-1,3-dihydroindol-2-one derivatives according to the present invention have an affinity for the vasopressin and oxytocin receptors.

Vasopressin is a hormone known for its antidiuretic effect and its effect in the regulation of arterial pressure. It stimulates several types of receptors, namely $V_1$ ($V_{1a}$, $V_{1b}$) and $V_2$. These receptors are localized in the liver, vessels (coronary, renal, cerebral), platelets, kidney, uterus, adrenal glands, central nervous system and pituitary gland. Oxytocin has a peptide structure similar to that of vasopressin. The oxytocin receptors are also found on the smooth muscle of the uterus, as well as on myoepithelial cells of the mammary gland, in the central nervous system and in the kidney. The localization of the different receptors is described in: S. JARS et al., Vasopressin and oxytocin receptors: an overview, in Progress in Endocrinology; H. IMURA and K. SHIZURNE ed., Experta Medica, Amsterdam, 1988, 1183–1188, and in the following articles: Presse Médicale, 1987, 16 (10), 481–485; J. Lab. Clin. Med., 1989, 114 (6), 617–632; and Pharmacol. Rev., 1991, 43 (1), 73–108. Vasopressin thus exerts cardiovascular, hepatic, antidiuretic and aggregating effects and effects on the central and peripheral nervous system and in the uterine domain. Oxytocin is involved in parturition, lactation and sexual behavior.

The compounds according to the present invention make it possible selectively either to mimic the effects of the hormone (in the case of agonists) or to inhibit them (in the case of antagonists). Vasopressin receptor antagonists can affect the regulation of the central and peripheral circulation, especially the coronary, renal and gastric circulation, as well as the regulation of hydration and the release of adrenocorticotrophic hormone (ACTH). Vasopressin agonists can advantageously replace vasopressin or its analogs in the treatment of diabetes insipidus; they can also be used in the treatment of enuresis and in the regulation of hemostasis: treatment of hemophilia and von Willebrand's syndrome, antidote to platelet aggregating agents, F. A. LASZLO, Pharmacol. Rev., 1991, 43, 73–108; and Drug Investigation, 1990, 2 (Suppl. 5), 1–47. The hormones themselves, namely vasopressin and oxytocin, and some of their peptide or non-peptide analogs are used in therapeutics and have been found to be effective. Several reviews and numerous literature articles may be mentioned: Vasopressin, P. GROSS et al. ed., John Libbey Eurotext, 1993, in particular 243–257 and 549–562; F. A. LASZLO and F. A. LASZLO Jr., Clinical perspectives for vasopressin antagonists, Drug News Perspect., 1993, 6 (8); W. G. NORTH, J. Clin. Endocrinol., 1991, 73, 1316–1320; J. J. LEGROS et al., Prog. Neuro-Pharmacol. Biol. Psychiat., 1988, 12, 571–586; K. E. ANDERSSON et al., Drugs Today, 1988, 24 (7), 509–528; D. L. STUMP et al., Drugs, 1990, 39, 38–53; S. CALTABIANO et al., Drugs Future, 1988, 13, 25–30; Y. MURA et al., Clin. Nephrol., 1993, 40, 60–61; and FASEB J., 1994, 8 (5), A 587:3398.

Thus the compounds according to the invention are useful especially in the treatment of complaints of the central and peripheral nervous system, the cardiovascular system, the renal domain and the gastric domain and in disorders of sexual behavior, in man and animals.

The present invention relates to compounds of the formula

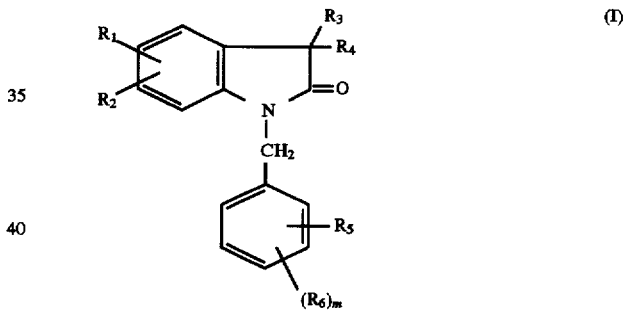

in which:

$R_1$ and $R_2$ are each independently a hydrogen; a halogeno; a hydroxyl; an ω-halogeno($C_1$–$C_7$)alkoxy; a ($C_1$–$C_7$) alkyl; a trifluoromethyl; a ($C_1$–$C_7$)alkoxy; a polyhalogeno ($C_1$–$C_7$)alkoxy; an ω-hydroxy($C_2$–$C_7$)alkoxy; an ω-methoxy($C_2$–$C_7$)alkoxy; an ω-amino($C_2$–$C_7$)alkoxy which is free or substituted by one or two ($C_1$–$C_7$)alkyls; a ($C_3$–$C_7$)cycloalkoxy; a ($C_3$–$C_7$)cycloalkylmethoxy; a phenoxy; a benzyloxy; a ($C_1$–$C_7$)alkylthio; a phenylthio; a nitro; an amino which is free or substituted by one or two ($C_1$–$C_7$)alkyls; a cyano; a formyl; a ($C_1$–$C_7$) alkylcarbonyl; a benzoyl; a formyloxy; a ($C_1$–$C_7$) alkylcarbonyloxy; a benzoyloxy; a ($C_1$–$C_7$) alkylsulfonamido; a phenylsulfonamido; a benzylsulfonamido; a ($C_1$–$C_7$)alkylcarbonylamino; a ($C_1$–$C_7$)alkoxycarbonylamino; a ureido which is unsubstituted or substituted by a phenyl, a benzyl or one or two ($C_1$–$C_7$)alkyls; or a thioureido which is unsubstituted or substituted by a phenyl, a benzyl or one or two ($C_1$–$C_7$) alkyls, with the proviso that $R_1$ and $R_2$ are not simultaneously hydrogen;

$R_3$ and $R_4$ together form a group —$(CH_2)_pX(CH_2)_q$—; or $R_3$ and $R_4$, together with the carbon to which they are bonded, form an optionally fused, saturated or unsaturated $C_3$–$C_{12}$ hydrocarbon ring which is unsubstituted or substituted by one or more ($C_1$–$C_7$)alkyl groups, by a $C_3$—$C_5$-spirocycloalkyl, by an oxo group or by one or two hydroxyls which are free or substituted by a group selected from the following: ($C_1$–$C_4$)alkyl, ($C_1$–$C_2$) alkoxy($C_1$–$C_4$)alkyl, phenyl($C_1$–$C_2$)alkoxy($C_1$–$C_4$)alkyl, tetrahydrofuranyl and tetrahydropyranyl;

$R_5$ is hydrogen or has one of the meanings designated for $R_6$;

$R_6$ is a halogen; a ($C_1$–$C_7$)alkyl; a trifluoromethyl; a cyano; a nitro; a hydroxylamino; a hydroxyl; a carboxyl; a guanidino which is unsubstituted or substituted in the 1-position by a ($C_1$–$C_7$)alkyl and/or in the 3-position by one or two ($C_1$–$C_7$)alkyls, a phenyl or a benzyl and/or in the 2-position by a cyano; a group —$OR_7$; a group —$SR_7$; a formyl; a ($C_1$–$C_7$)alkylcarbonyl; a benzoyl; a ($C_1$–$C_7$) alkoxycarbonyl; a phenoxycarbonyl; a benzyloxycarbonyl; a group —$CONR_{17}R_{18}$; a group —$CSNR_{11}R_{19}$; a group —$SO_2NR_{20}R_{21}$; a ($C_1$–$C_7$)alkylsulfonamido; a group —$NHSO_2$—Ar; a benzylsulfonamido; an aminosulfonamido in which the amino is free or substituted by $R_{16}$ and $R_{22}$; a group —$NR_8R_9$; a group —CO—NH— $CR_{10}R_{23}$—$COR_{12}$; or a group —$CH_2NR_8R_9$;

$R_7$ is a ($C_1$–$C_7$)alkyl; a phenyl; a benzyl; a ($C_3$–$C_7$) cycloalkyl; a ($C_2$–$C_7$)alkenyl; an ω-halogeno($C_2$–$C_7$) alkyl; a polyhalogeno($C_1$–$C_7$)alkyl; an ω-hydroxy ($C_2$–$C_7$)alkyl; a formyl; a ($C_1$–$C_7$)alkylcarbonyl; a benzoyl; an ω-carboxy($C_1$–$C_7$)alkyl; an ω-($C_1$–$C_7$) alkoxycarbonyl($C_1$–$C_7$)alkyl; an ω-benzyloxycarbonyl ($C_1$–$C_7$)alkyl; an ω-amino($C_2$–$C_7$)alkyl in which the amino group is free or substituted by one or two ($C_1$–$C_7$) alkyls, or in the form of an ammonium ion; or an ω-carbamoyl($C_1$–$C_7$)alkyl in which the carbamoyl is free or substituted by one or two ($C_1$–$C_7$)alkyls;

$R_8$ and $R_9$ are each independently a hydrogen; a ($C_1$–$C_7$) alkyl; or a group —$CH_2$—Ar; $R_9$ can also be a group Ar; a ($C_3$–$C_8$)alkenyl; a formyl; a ($C_1$–$C_7$)alkyl carbonyl; a ($C_1$–$C_7$)alkylthiocarbonyl; a ($C_3$–$C_7$)cycloalkylcarbonyl; a ($C_3$–$C_7$)cycloalkylthiocarbonyl; an ω-amino($C_2$–$C_7$) alkylcarbonyl in which the amino is free or substituted by one or two ($C_1$–$C_7$)alkyls; an ω-hydroxy($C_1$–$C_7$) alkylcarbonyl; an ω-benzyloxy($C_1$–$C_7$)alkylcarbonyl; a pyridylcarbonyl; a methylpyridylcarbonyl; thienylcarbonyl; a group —CO—Ar; a group —CO—$CH_2$—Ar; ($C_1$–$C_7$)alkoxycarbonyl; a phenoxycarbonyl; a phenoxythiocarbonyl; a benzyloxycarbonyl; a group —CO—$CR_{10}R_{23}$—$NR_{11}R_{19}$; a group —$CR_{10}R_{23}COR_{12}$; a group —$(CH_2)_xCOR_{12}$; a group —$CO(CH_2)_xCOR_{12}$; a group —$CONR_{14}R_{24}$; a group —$CSNR_{14}R_{24}$; or a heterocyclic radical selected from pyrazolyl, imidazolyl, triazolyl, tetrazolyl, pyridyl, pyridazinyl, pyrimidinyl and thiazolyl;

or else $R_8$ and $R_9$, together with the nitrogen atom to which they are bonded, form hydantoin; N-methylhydantoin; or a heterocyclic radical selected from pyrrol-1-yl, Δ3-pyrrolin-1-yl, pyrrolidin-1-yl isoindolin-2-yl in which the benzene ring unsubstituted or substituted by a halogen, a ($C_1$–$C_7$)alkyl, a trifluoromethyl or a methoxy;

$R_{10}$ and $R_{23}$ are each independently hydrogen; a ($C_1$–$C_7$) alkyl; or a benzyl;

or $R_{10}$ and $R_{23}$, together with the carbon atom to which they are bonded, form a ($C_3$–$C_7$)cycloalkyl;

$R_{11}$ and $R_{19}$ are each independently hydrogen; or a ($C_1$–$C_7$) alkyl;

$R_{12}$ is a hydroxyl; a ($C_1$–$C_7$)alkoxy; or an amino which is free or substituted by one or two ($C_1$–$C_7$)alkyls;

$R_{13}$ is hydrogen; a ($C_1$–$C_7$)alkyl; a phenyl; a benzyl; a formyl; a ($C_1$–$C_7$)alkylcarbonyl; a benzoyl; a ($C_1$–$C_7$) alkoxycarbonyl; or a carbamoyl which is unsubstituted or substituted by one or two ($C_1$–$C_7$)alkyls;

$R_{14}$ and $R_{24}$ are each independently hydrogen; or a ($C_1$–$C_7$) alkyl; $R_{24}$ can also be a ($C_1$–$C_7$)alkyl substituted by $R_{15}$; a group Ar; a ($C_3$–$C_7$)cycloalkyl; or an adamantyl;

or $R_{14}$ and $R_{24}$, together with the nitrogen atom to which they are bonded, form a heterocycle selected from morpholine, thiomorpholine, piperazine, azetidine, pyrrolidine, piperidine and perhydroazepine, said heterocycle being unsubstituted or substituted by one or more methyl groups, a phenyl or an amino group which is free or carries a protecting group;

$R_{15}$ is a group Ar; a pyridyl; a hydroxyl; a ($C_1$–$C_7$)alkoxy; a group —$NR_{11}R_{19}$; a carboxyl; or a ($C_1$–$C_7$) alkoxycarbonyl;

$R_{16}$ and $R_{22}$ are each independently a hydrogen; or a ($C_1$–$C_7$)alkyl;

or $R_{16}$ and $R_{22}$, together with the nitrogen aton to which they are bonded, form a heterocycle selected from azetidine, pyrrolidine, piperidine, piperazine and perhydroazepine, said heterocycle being unsubstituted or substituted by one or more methyl groups;

$R_{17}$ and $R_{18}$ are each independently hydrogen; or a ($C_1$–$C_8$) alkyl; $R_{18}$ can also be a ($C_3$–$C_7$)cycloalkyl which is unsubstituted or substituted by a ($C_1$–$C_4$)alkyl; a group Ar; a pyridyl; a methylpyridyl; a piperid-4-yl substituted in the 1-position by $R_{27}$; a piperid-1-yl; a pyrrolidin-1-yl; a morpholin-4-yl; or a ($C_1$–$C_7$)alkyl substituted by one or more halogens or by $R_{26}$;

or else $R_{17}$ and $R_{18}$, together with the nitrogen atom to which they are bonded, form a heterocyclic radical $R_{25}$;

$R_{20}$ and $R_{21}$ are each independently hydrogen; or a ($C_1$–$C_7$) alkyl;

or else $R_{20}$ and $R_{21}$, together with the nitrogen atom to which they are bonded, form a heterocyclic radical $R_{25}$;

$R_{25}$ is a morpholin-4-yl; a thiomorpholin-4-yl; an azetidin-1-yl which is unsubstituted or substituted in the 3-position by a group -$NR_{11}R_{19}$, a ($C_1$–$C_7$)alkyl, a phenyl, a benzyl, or a ($C_1$–$C_7$)alkylcarbonyl; a perhydroazepin-1-yl; a piperazin-1-yl which is unsubstituted or substituted in the 4-position by a ($C_1$–$C_7$)alkyl, a phenyl, a benzyl, a ($C_1$–$C_7$)alkylcarbonyl, a ($C_1$–$C_7$)alkoxycarbonyl or a benzyloxycarbonyl; a piperid-1-yl which is unsubstituted or substituted in the 4-position by a ($C_1$–$C_7$)alkyl, a phenyl, a benzyl, a ($C_1$–$C_7$)alkylcarbonyl or a group —$NR_{11}R_{19}$; or a pyrrolidin-1-yl which is unsubstituted or substituted by a ($C_1$–$C_7$)alkyl, a phenyl, a benzyl, a ($C_1$–$C_7$)alkylcarbonyl, a hydroxymethyl, a carboxyl, a ($C_1$–$C_7$)alkoxycarbonyl or a carbamoyl which is unsubstituted or substituted by one or two ($C_1$–$C_7$)alkyls;

$R_{26}$ is a hydroxyl; a ($C_1$–$C_7$)alkoxy; a cyano; a carboxyl; a ($C_1$–$C_7$)alkoxycarbonyl; a benzyloxycarbonyl; a group —$NR_{11}R_{19}$; a carbamoyl which is free or substituted by one or two ($C_1$–$C_7$)alkyls; a pyrrolidin-1-ylcarbonyl; a piperid-1-ylcarbonyl; a perhydroazepin-1-ylcarbonyl; a group Ar; a ($C_3$–$C_7$)cycloalkyl; an adamantyl; or a heterocyclic radical selected from a pyridyl, a methylpyridyl, a furanyl, a tetrahydrofuranyl, a thienyl, a methylthienyl, a pyrrolidin-1-yl, a piperid-1-yl and a perhydroazepin-1-yl;

$R_{27}$ is a hydrogen; a ($C_1$–$C_7$)alkyl; a phenyl; a benzyl; a formyl; a ($C_1$–$C_7$)alkylcarbonyl; a benzoyl; a ($C_1$–$C_7$) alkoxycarbonyl; a phenoxycarbonyl; or a carbamoyl which is free or substituted by one or two ($C_1$–$C_7$)alkyls;

Ar is a phenyl which is unsubstituted or monosubstituted or polysubstituted by a substituent selected from a halogen atom, a ($C_1$–$C_7$)alkyl, a trifluoromethyl, a hydroxyl, a ($C_1$–$C_7$)alkoxy, a carboxyl, a ($C_1$–$C_7$)alkoxycarbonyl, a ($C_1$–$C_7$)alkylcarbonyloxy, a nitro, a cyano, an amino, a ($C_1$–$C_7$)alkylamino and a ($C_1$–$C_7$)dialkylamino, said substituents being identical or different;

m is 1 or, if $R_6$ is a halogen, a ($C_1$–$C_7$)alkyl or a ($C_1$–$C_7$) alkoxy, m can also be 2, 3 or 4, or else $(R_6)_m$ can be m substituents having different meanings selected from halogen, ($C_1$–$C_7$)alkyl and ($C_1$–$C_7$)alkoxy;

p and q are each an integer, it being possible for their sum to vary from 3 to 6;

t is an integer which can vary from 2 to 5;

u is an integer which can vary from 0 to 3;

X is oxygen, a group —$NR_{13}$, a group —$N(O)R_{13}$ or a group $S(O)_x$; and x is 0, 1 or 2;

and their salts where appropriate.

If a compound according to the invention has one or more asymmetric carbons, the invention includes all the optical isomers of this compound.

The salts of the compounds of formula (I) according to the present invention include those with mineral or organic acids which permit a suitable separation or crystallization of the compounds of formula (I), such as picric acid, oxalic acid or an optically active acid, for example a mandelic acid or a camphosulfonic acid, and mineral or organic acids which form physiologically acceptable salts such as the hydrochloride, hydrobromide, sulfate, hydrogensulfate, dihydrogenphosphate, maleate, fumarate and naphthalene-2-sulfonate.

The salts of the compounds of formula (I) also include those with organic or mineral bases, for example the salts with alkali metals or alkaline earth metals, such as the sodium, potassium and calcium salts, the sodium and potassium salts being preferred, or with an amine such as trometamol, or else those with arginine, lysine or any physiologically acceptable amine.

According to the present invention, halogen is understood as meaning an atom selected from fluorine, chlorine, bromine and iodine, preferably fluorine or chlorine.

According to the present invention, amino-protecting group is understood as meaning a group such as a ($C_1$–$C_4$) alkyl, for example a methyl or a tert-butyl; a benzyl; a substituted benzyl such as p-nitrobenzyl, p-chlorobenzyl or p-methoxybenzyl; a benzhydryl; a trityl; a benzoyl; a ($C_1$–$C_4$)alkylcarbonyl, for example an acetyl; a ($C_1$–$C_4$) alkoxycarbonyl, for example a methoxycarbonyl, an ethoxycarbonyl or a tert-butoxycarbonyl; or a benzyloxycarbonyl.

According to the present invention, $C_1$–$C_7$-, $C_1$–$C_8$- or $C_1$–$C_4$-alkyl is understood as meaning a linear or branched $C_1$–$C_7$-, $C_1$–$C_8$- or $C_1$–$C_4$-alkyl. $C_1$–$C_7$- or $C_1$–$C_4$-alkoxy is understood as meaning a linear or branched $C_1$–$C_7$- or $C_1$–$C_4$-alkoxy.

According to the present invention, optionally fused, saturated or unsaturated $C_3$–$C_{12}$ hydrocarbon ring is understood as meaning a variety of hydrocarbon rings of monocyclic, bicyclic or tricyclic structure, for example a cyclobutane, a cyclopentane, a cyclohexane, a cycloheptane, a cyclooctane, an indane, a hexahydroindane, an adamantane, a norbornane, a norbornene, a dihydrophenalene, a tricyclo[5.2.1.0$^{2,6}$]decane or a tricyclo [5.2.1.0$^{2,6}$]dec-8-ene, a bicyclo[2.2.1]heptane or a bicyclo [3.3.1]nonane.

The compounds of formula (I) in which $R_1$ is in the 5-position of the 1,3-dihydroindol-2-one and $R_2$ is hydrogen are preferred compounds.

The compounds of formula (I) in which $R_1$ is a chlorine or fluorine atom or an ethoxy group in the 5-position of the 1,3-dihydroindol-2-one and $R_2$ is hydrogen are preferred compounds.

The compounds of formula (I) in which $R_3$ and $R_4$, together with the carbon to which they are bonded, form a $C_3$–$C_{12}$ hydrocarbon ring are preferred compounds; particularly preferred compounds are those in which $R_3$ and $R_4$, together with the carbon to which they are bonded, form a cycloheptane, an adamantane, a tricyclo[5.2.1.0$^{2,6}$]dec-8-ene, a tricyclo[5.2.1.0$^{2,6}$]decane, a bicyclo[2.2.1]heptane, a bicyclo[3.3.1]nonane or a cyclohexane which is unsubstituted or substituted by a $C_3$–$C_5$-spirocycloalkyl, by one or two $C_1$–$C_7$-alkyl groups or by a $C_1$–$C_4$-alkoxy.

Very particularly preferred compounds of formula (I) are those in which $R_3$ and $R_4$, together with the carbon to which they are bonded, form a tricyclo[5.2.1.0$^{2,6}$]decane or a tricyclo[5.2.1.0$^{2,6}$]dec-8-ene.

The compounds of formula (I) in which $R_3$ and $R_4$, together with the carbon to which they are bonded, form a piperidine-4 ring which is unsubstituted or substituted on the nitrogen by a $C_1$–$C_7$-alkyl are also preferred.

The compounds of formula (I) in which $R_5$ is either hydrogen or a methoxy group in the 2-position and $R_6$ in the 4-position is a group —$NR_8R_9$ in which $R_8$ and $R_9$ are as hereinabove defined are also preferred compounds of the invention.

Particularly preferred are the compounds of formula (I) in which $R_5$ is either hydrogen or a methoxy group in the 2-position and $R_6$ in the 4-position is a methoxy, a ($C_1$–$C_7$) alkylcarboxamido, a group —NHCO—Ar, a group —$CONR_{17}R_{18}$ or a group —$NR_8CONR_{14}R_{24}$, in which the substituents Ar, $R_{17}$, $R_{18}$, $R_8$, $R_{14}$ and $R_{24}$ are as defined above for the compounds of formula (I).

The following abbreviations are used in the description and in the Examples:

DCM: dichloromethane
ether: ethyl ether
iso ether: isopropyl ether
Boc: tert-butoxycarbonyl
Me, MeO: methyl, methoxy
Et, OEt: ethyl, ethoxy
Pr, iPr, nPr: propyl, isopropyl, n-propyl
Bu, iBu, tBu: butyl, isobutyl, tert-butyl
Ts: tosyl
Ph: phenyl
Bz: benzyl
Ac: acetyl
AcOEt: ethyl acetate
AcOH: acetic acid
MeOH: methanol
EtOH: ethanol
DMF: dimethylformamide
THF: tetrahydrofuran
DMSO: dimethyl sulfoxide
DIPEA: diisopropylethylamine
TEA: triethylamine
TFA: trifluoroacetic acid
TMEDA: tetramethylethylenediamine
BOP: benzotriazol-1-yloxytris (dimethylaminophosphonium) hexafluorophosphate
Lawesson's reagent: 2,4-bis(4-methoxyphenyl)-1,3-dithia-2,4-diphosphetane 2,4-disulfide
M.p.: melting point
saline solution: water saturated with sodium chloride
TLC: thin layer chromatography
HPLC: high pressure liquid chromatography
aqueous hydrochloric acid: dilute hydrochloric acid, about 1N
RT: room temperature The present invention further relates to a process for the preparation of the compounds according to the invention, which comprises:

a) reacting a benzyl halide of the formula:

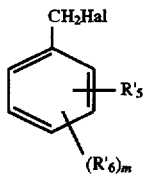 (III)

in which Hal is a halogen atom, preferably bromine or chlorine, and R'$_5$ and R'$_6$ are respectively either R$_5$ and R$_6$ as defined above for (I), or precursor groups of R$_5$ and R$_6$, with a 1,3-dihydroindol-2-one disubstituted in the 3-position of the formula:

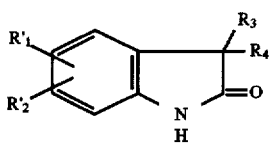 (II)

in which R'$_1$ and R'$_2$ are respectively either R$_1$ and R$_2$ as defined for (I), or precursor groups of R$_1$ and R$_2$, and R$_3$ and R$_4$ are as defined above for (I); and b) either, if R'$_1$=R$_1$, R'$_2$=R$_2$, R'$_5$=R$_5$ and R'$_6$=R$_6$, isolating the resulting compound of formula (I);

c) or, if any one of the groups R'$_1$, R'$_2$, R'$_5$ and/or R'$_6$ is respectively a precursor group of R$_1$, R$_2$, R$_5$ and/or R$_6$, subjecting the compound obtained in step a), hereafter called compound (I'), to a subsequent treatment in order to prepare the compound of formula (I) by converting any one of the groups R'$_1$, R'$_2$, R'$_5$ and/or R'$_6$ to R$_1$, R$_2$, R$_5$ and/or R$_6$ respectively.

The reaction of step a) is carried out in an anhydrous solvent such as DMF or THF, in the presence of a metal hydride such as, for example, sodium hydride, or in the presence of an alcoholate such as potassium tert-butylate.

The 1,3-dihydroindol-2-ones (II) are known or can be prepared by known methods according to different procedures.

Compounds (II) in which R'$_1$ and/or R'$_2$ are a halogen and R$_3$ and R$_4$, together with the carbon to which they are bonded, form a spirocyclobutane, a spirocyclohexane or a spirocycloheptane are known, for example from D. W. Robertson et al., J. Med. Chem., 1987, 30 (5), 824–829. Furthermore, 5-chloro-3-spirocyclopentaneindol-2-one is described in U.S. Pat. No. 3,947,451.

To prepare the compounds (II) in the case where R$_3$ and R$_4$ together are a hydrocarbon group, it is possible to use Brunner's reaction described by R. F. Moore and S. G. P. Plant in J. Chem. Soc., 1951, 3475–3478, which leads to the preparation of compounds (II) in which CR$_3$R$_4$ is a cyclopentane or a cyclohexane.

This reaction is carried out by cyclizing a phenylhydrazide derivative of the formula:

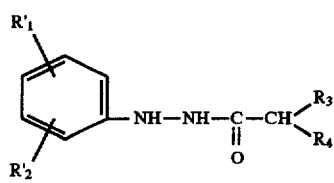 (IV)

in which R'$_1$ and R'$_2$ are as defined above for (II) and R$_3$ and R$_4$ are as defined above for (I), for example by heating in quinoline in the presence of calcium oxide.

According to the same authors, the phenylhydrazide derivative (IV) is obtained by reacting a hydrazine derivative of the formula:

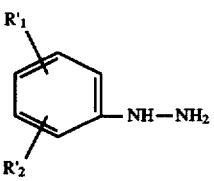 (V)

in which R'$_1$ and R'$_2$ are as defined above for (II), with an acid halide of the formula:

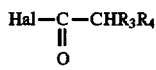 (VI)

in which R$_3$ and R$_4$ are as defined above for (I).

In one particular embodiment, if R$_3$ and R$_4$, together with the carbon to which they are bonded, form a polycondensed hydrocarbon ring, for example a norbornane or a norbornene, the method described by J. Wolff et al., Tetrahedron, 1986, 42 (15), 4267–4272, is used: First of all a lithium salt of the compound (IV) is prepared by reaction with a lithium reagent such as n-butyllithium, in an inert solvent such as THF, at low temperature, and said salt is then cyclized by heating in a solvent such as naphthalene or prehnitene (1,2,3,4-tetramethylbenzene).

The compounds (II) in which R'$_1$=R'$_2$=H and CR$_3$R$_4$ is adamantane are described by I. Fleming et al., J. Chem. Soc., Perkin Trans. I, 1991, 3, 617–626. The compounds (II) in which R$_3$ and R$_4$, together with the carbon atom to which they are bonded, form an adamantane and R'$_1$ and R'$_2$ are other than hydrogen can be prepared by the method described above.

The hydrazine derivatives (V) are known or prepared by known methods. The same applies to the acid halides (VI).

A 1,3-dihydroindol-2-one disubstituted in the 3-position (II) can also be prepared from a 1,3-dihydroindol-2-one of the formula:

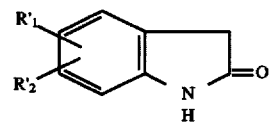 (VII)

in which R'$_1$ and R'$_2$ are as defined above for (II), by using various processes.

For example, the addition of an alkylating agent is effected in an appropriate solvent by the method described by A. S. Kende and J. C. Hodges in Synth. Commun., 1982, 12 (1), 1–10. Thus, to prepare a compound (II) in which R$_3$ and R$_4$ together form a group of the formula —(CH$_2$)$_n$—, where n varies from 3 to 12, the reagent used is a compound of the formula Z(CH$_2$)$_n$Z, in which Z is an electrophilic group such as a halogen, preferably bromine or iodine, a tosyloxy group or a mesyloxy group.

The compounds (II) in which R$_3$ and R$_4$, together with the carbon to which they are bonded, form a C$_4$–C$_8$ hydrocarbon ring substituted by one or more C$_1$–C$_7$-alkyl groups or by a C$_3$–C$_5$-spirocycloalkyl are prepared in the same way.

If R$_3$ and R$_4$ together form a group —(CH$_2$)$_p$X(CH$_2$)$_q$—, in which p, q and X are as defined above for (I), a 1,3-dihydroindol-2-one disubstituted in the 3-position of formula (II) can be prepared from a 1,3-dihydroindol-2-one unsubstituted in the 3-position (VII) by reaction with a compound of the formula

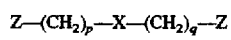 Z—(CH$_2$)$_p$—X—(CH$_2$)$_q$—Z (VIII)

in which Z is as defined above and X, p and q are as defined above for (I). The reaction is carried out in the presence of an alcoholate, for example potassium tert-butylate, in an anhydrous solvent such as, for example, THF.

If X is a nitrogen atom substituted by a formyl, a $(C_1-C_7)$alkylcarbonyl, a benzoyl, a $(C_1-C_7)$alkoxycarbonyl or an $N-(C_1-C_7)$alkylcarbamoyl, the substitution on X can be effected either on the 1,3-dihydroindol-2-one derivative (II) or on the final compound (I) starting from a compound in which the nitrogen atom (X=NH) is unsubstituted.

Thus, if X is a nitrogen atom substituted by a $(C_1-C_7)$ alkoxycarbonyl, the first step is to prepare a compound (II) or (I) in which X is NH, which is then reacted with the appropriate chloroformate to give the desired compound (II) or (I). In the same way, a $C_1-C_7$-alkyl isocyanate is reacted with a compound (II) or (I) in which X=NH to give a derivative (II) or a compound (I) in which X is a nitrogen atom substituted by an $N-(C_1-C_7)$alkylcarbamoyl. The formic acid in the presence of acetic anhydride or respectively an acid chloride or an anhydride is reacted with a compound (II) or a compound (I) in which X=NH in order to prepare a compound of formula (II) or respectively a compound of formula (I) in which X is a nitrogen atom substituted by a formyl, a $(C_1-C_7)$alkylcarbonyl or a benzoyl.

If X is a sulfur atom or a nitrogen atom substituted by $R_{13}$, it is also possible firstly to prepare a compound of the formula:

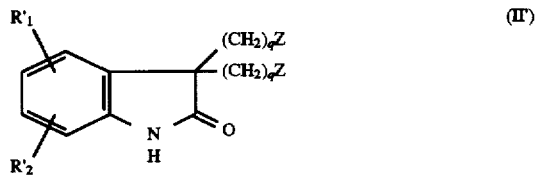

(II')

in which $R'_1$, $R'_2$, Z, p and q are as defined above, and to perform a nucleophilic substitution with a hydrogen sulfide salt or an amine of the formula $H_2NR_{13}$, in a solvent such as an alcohol, an ether, DMF or a mixture thereof, at a temperature between 5° C. and the reflux temperature.

The 1,3-dihydroindol-2-ones of formula (II') are obtained from the corresponding diols protected for example by a tetrahydropyran-2-yl group. The reaction can be carried out with dibromotriphenylphosphorane according to J. Chem. Soc., Chem. Commun., 1989, 1619.

The compounds (II) in which $R_3$ and $R_4$, together with the carbon to which they are bonded, form a pyrrolidine, N-alkylpyrrolidine, piperidine or N-alkylpiperidine ring are described by M. J. Kornet in J. Med. Chem., 1976, 19 (7), 892–899.

In particular, horsfiline of the formula:

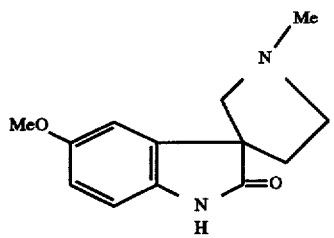

is an alkaloid described in A. Jossang et al., J. Chem., 1991, 56 (23), 6527–6530.

To prepare a compound of formula (II) in which $R_3$ and $R_4$, together with the carbon to which they are bonded, form a tricyclo[5.2.1.0$^{2,6}$]decane or a tricyclo[5.2.1.0$^{2,6}$]dec-8-ene, a compound (VII') or, respectively, a compound (VII") of the formulae

(VII')

(VII")

in which Z is as defined above, is reacted with a compound of formula (VII). Compounds (VII') and (VII") substituted by one or more $C_1-C_7$-alkyl groups are used to prepare compounds (II) in which said carbocycles are substituted.

A compound of formula (II) in which $R_3$ and $R_4$, together with the carbon to which they are bonded, form a tricyclo [5.2.1.0$^{2,6}$]decane can also be prepared by the catalytic hydrogenation of a compound of formula (II) in which $R_3$ and $R_4$, together with the carbon to which they are bonded, form a tricyclo[5.2.1.0$^{2,6}$]dec-8-ene, for example in the presence of palladium-on-charcoal or Raney® nickel.

A compound of formula (I) in which $R_3$ and $R_4$, together with the carbon to which they are bonded, form a tricyclo [5.2.1.0$^{2,6}$]decane can also be prepared by the catalytic hydrogenation of a compound of formula (I) in which $R_3$ and $R_4$, together with the carbon to which they are bonded, form a tricyclo[5.2.1.0$^{2,6}$]dec-8-ene, for example in the presence of palladium-on-charcoal or Raney® nickel.

To prepare a compound (II) in which $R_3$ and $R_4$, together with the carbon to which they are bonded, form an indane or a hexahydroindane, a compound (VIII') or, respectively, a compound (VIII") of the formulae:

(VIII')

(VIII")

in which Z is defined as indicated above for (VIII), is reacted with a compound (VII). Compounds (VIII') and (VIII") substituted by one or more $C_1-C_7$-alkyl groups are used to prepare compounds (II) in which the indane or hexahydroindane is substituted.

In the same way, the method of A. S. Kende and J. C. Hodges described above is used to prepare compounds of formula (II) in which the substituents $R_3$ and $R_4$, together with the carbon to which they are bonded, form a saturated or unsaturated $C_3-C_{12}$ hydrocarbon ring substituted by one or more $(C_1-C_7)$alkyl groups or by a group selected from an oxo group, a $C_3-C_5$-spirocycloalkyl, a hydroxyl substituted by a $(C_1-C_7)$alkyl, a $(C_1-C_2)$alkoxy$(C_1-C_4)$alkyl, a phenyl $(C_1-C_2)$alkoxy$(C_1-C_4)$alkyl, a tetrahydrofuranyl and a tetrahydropyranyl. To obtain the compounds of formula (I) in which $R_3$ and $R_4$, together with the carbon to which they are bonded, form a saturated or unsaturated $C_3-C_{12}$ hydrocarbon ring substituted by a hydroxyl, the corresponding compounds of formula (I) in which the hydroxyl group is substituted by a $(C_1-C_2)$alkoxy$(C_1-C_4)$alkyl, a tetrahydrofuranyl or a tetrahydropyranyl are deprotected. This deprotection is effected in an acid medium, for example in the presence of a mineral or organic acid, in an alcohol or ether solvent such as THF, at a temperature between 15° C. and the reflux temperature; the deprotection can be carried out for example in the presence of hydrochloric acid or pyridinium toluenesulfonate in an alcohol.

The compounds of formula (II) in which $R_3$ and $R_4$, together with the carbon to which they are bonded, form either an optionally fused, saturated or unsaturated $C_3-C_{12}$ hydrocarbon ring substituted by an oxo group, or a group —$(CH_2)_p$—X—$(CH_2)_q$— in which X is a group SO, $SO_2$ or $N(O)R_{13}$, are prepared by known oxidation reactions starting from the corresponding compounds of formula (II) in which $R_3$ and $R_4$, together with the carbon atom to which they are bonded, respectively form either an optionally fused, saturated or unsaturated $C_3-C_{12}$ hydrocarbon ring substituted by a hydroxyl, or a group —$(CH_2)_p$—X—$(CH_2)_q$— in which X is a sulfur atom or a group $NR_{13}$.

For example, the oxidation of secondary alcohols to ketones can be carried out in the presence of chromium oxide complexes such as pyridinium chlorochromate, in an inert solvent such as methylene chloride, or with oxidizing agents such as DMSO, by the methods described in Tetrahedron, 1978, 34, 1651–1660.

The oxidation of the compounds (II) containing a sulfur or nitrogen atom (X=S, $NR_{13}$) can be effected in the presence of hydrogen peroxide or peracids such as peracetic or metachloroperbenzoic acid, in inert solvents such as ketones or acetic acid, at temperatures between 0° C. and 50° C.

The derivatives (VII) are known or are prepared by known methods. An example which may be cited is J. V. RajanBabu in J. Org. Chem., 1986, 51, 1704–1712.

The compounds of formula (II) which carry certain substituents $R'_1$ and $R'_2$ on their benzene moiety are used as precursors for the preparation of compounds of formula (II) which carry other substituents $R'_1$ and $R'_2$. For example, the compounds (II) in which $R'_1$ and/or $R'_2$=H can be nitrated with the conventional reagents; they can also be acylated by reaction with an acid chloride of the formula RCOCl, in which R is a $C_1-C_7$-alkyl, in the presence of a Lewis acid such as aluminum chloride, in order to prepare a compound (II) in which $R'_1$ and/or $R'_2$=—COR. The compound (II) in which $R'_1$ is an amino group is prepared by the catalytic hydrogenation of a compound (II) in which $R'_1$ is a nitro group and $R'_2$ is hydrogen.

The halides of formula (III) are known or are prepared by known methods.

Publications describing the following halogenomethylbenzene derivatives may be cited by way of example:

1,2,4-, 4,2,1- or 2,4,1-chloromethylmethyl methoxybenzene: Bull. Soc. Chim. France, 1937, 4, 1092.

2-Chloromethyl-1,3-dimethoxybenzene: Chem. Listy, 1953, 47, 601–612.

1-Bromomethyl-2-methoxy-4-nitrobenzene: Sci. Sinica (Peking), 1962, 11, 483–498.

1-Bromomethyl-2-methyl-4-nitrobenzene: Pharmazie, 1969, 24 (1), 29–32.

1-Bromomethyl-2-methoxy-4-nitrobenzene: Bull.Soc. Chim. France, 1962, 2255.

1-Bromomethyl-4-methoxy-2-nitrobenzene: Zh. Obshch. Khim., 1963, 33 (8), 2792–2793.

Methyl 4-bromomethyl-3-methoxybenzoate: European patent application EP 179 619.

Ethyl 2-bromomethyl-6-methoxybenzoate: J. Org. Chem., 1983, 48, 3439–3444.

Ethyl 2-Bromomethyl-4,5-dimethoxybenzoate and ethyl 2-bromomethyl-3,4-dimethoxybenzoate: J. Org. Chem., 1968, 33, 494.

Methyl 4-bromomethyl-2-methoxybenzoate: Bull. Soc. Chim. France, 1962, 2255.

1-Bromomethyl-4-cyano-2-methoxybenzene: J. Med. Chem., 1990, 33, 2437–2451.

In general, the halogenomethylbenzene derivatives can be prepared by reacting N-bromosuccinimide with the corresponding methylbenzene derivatives. The reaction is carried out in a solvent such as carbon tetrachloride, in the presence of dibenzoyl peroxide. A halogenomethylbenzene derivative can also be prepared from a corresponding hydroxymethylbenzene derivative by reaction with phosphorus tribromide in ether.

In another process, the halogenomethylbenzene derivatives of formula (III) can be prepared from the corresponding alcohol by reaction with thionyl chloride in order to prepare a methylbenzene chloride.

For certain meanings of the substituents $R_1$, $R_2$, $R_5$ and/or $R_6$, the compounds (I) according to the invention can be prepared from a precursor of formula (I') substituted by a group $R'_1$, $R'_2$, $R'_5$ and/or $R'_6$, called a precursor group of $R_1$, $R_2$, $R_5$ and/or $R_6$, using methods known to those skilled in the art.

The following description relates to the preparation of the compounds of formula (I) carrying substituents $R_1$ and/or $R_6$; the same methods are applied to the preparation of the compounds in which the substituents $R_2$ and/or $R_5$ have the meanings indicated for $R_1$ and/or $R_6$.

The compounds (I) in which $R_1$ and/or $R_6$ is a hydroxyl can be obtained by the catalytic hydrogenation of a compound of formula (I') in which $R'_1$ and/or $R'_6$ if a benzyloxy, for example in the presence of palladium-on-charcoal. These compounds can also be prepared from analogous compounds of formula (I') in which $R'_1$ and/or $R'_6$ is an amino group by using the method described in J. Org. Chem., 1977, 42, 2053.

The compounds of formula (I) in which $R_1$ and/or $R_6$ is a $(C_1-C_7)$alkoxy can be prepared directly by the process according to the invention starting from the correctly substituted compounds of formulae (II) and (III).

The compounds (I') in which $R'_1$ and/or $R'_6$ is a hydroxyl can also be used to prepare compounds (I) in which $R_1$ and/or $R_6$ is a $(C_1-C_7)$alkoxy by reaction with a $C_1-C_7$-alkyl halide in the presence of a base such as a metal hydride or an alkali metal or alkaline earth metal carbonate like $K_2CO_3$ or $Cs_2CO_3$, in a solvent such as THF or DMF. Likewise, the compounds of formula (I) in which $R_1$ and/or $R_6$ is an ω-aminoalkoxy are prepared by reacting an ω-chloroalkylamine with the compounds in which $R'_1$ and/or $R'_6$=OH; again, the compounds in which $R_1$ and/or $R_6$ is an ω-hydroxyalkoxy are prepared by reaction with a chloroalkyl alcohol ; in the particular case of the preparation of a compound (I) in which $R_1$ and/or $R_6$=—O($CH_2$)$_2$OH, it is also possible to react ethylene carbonate with a compound (I') in which $R'_1$ and/or $R'_6$=—OH.

The halogenoalkoxybenzyl halides (III, $R'_6$=ω-halogenoalkoxy) are used for the preparation of compounds according to the invention in which the substituent $R_6$ is an ω-aminoalkoxy which is unsubstituted or substituted by one or two alkyls, according to the following equation:

in which Alk' is a $(C_2-C_7)$alkyl and A and A' independently of one another are H or a $(C_1-C_7)$alkyl.

The compounds of formula (I) in which $R_1$ and/or $R_6$ is a formyloxy, a $(C_1-C_7)$alkylcarbonyloxy or a benzoyloxy are obtained by reacting for example, the formic acid in the presence of dicyclohexylcarbodiimide (J. HUANG et al. J. Chem. Research (S), 1991, 292–293) or respectively by reacting an acid halide or an anhydride with a compound (I') in which $R'_1$ and/or $R'_6$ is a hydroxyl.

The compounds of formula (I) in which $R_6$ is a group —$OR_7$, $R_7$ being an ω-carbamoyl($C_1-C_7$)alkyl which is free or substituted by one or two $C_1$–$C_7$-alkyls, can be prepared from a compound (I') in which $R'_6$ is a group —$OR_7$, $R_7$ being an ω-carboxy($C_1$–$C_7$)alkyl esterified by a $C_1$–$C_7$-alkyl. This preparation is carried out in a manner conventional to those skilled in the art by reaction with a correctly chosen amine.

The compounds of formula (I) in which $R_6$ is a ($C_1$–$C_7$) alkoxycarbonyl can be prepared directly by the process according to the invention. Using methods known to those skilled in the art, they make it possible to obtain the compounds of formula (I) in which $R_6$ is a carboxyl group.

The compounds of formula (I') in which $R'_6$ is a benzyloxycarbonyl make it possible, by catalytic hydrogenation, to obtain the compounds (I) in which $R_6$ is a carboxyl. Reaction with a thionyl halide gives the compounds of formula (I') in which $R'_6$ is a halogenocarbonyl. Such compounds are reacted with a compound $HNR_{17}R_{18}$ in order to prepare compounds of formula (I) in which $R_6$ is a carbamoyl substituted by $R_{17}$ and $R_{18}$. The compounds of formula (I') in which the substituent $R'_6$ is a phenoxycarbonyl can also be used to obtain the compounds of formula (I) in which $R_6$ is a phenylcarbamoyl or a ($C_1$–$C_7$) alkylcarbamoyl by reaction with an aniline or a ($C_1$–$C_7$) alkylamine. An aniline substituted on the phenyl by anyone of the phenyl substituents as defined for Ar, or an alkylamine substituted on the alkyl by $R_{26}$ makes it possible to obtain compounds of formula (I) in which $R_6$ is a phenylcarbamoyl substituted on the phenyl or, respectively, an alkylcarbamoyl substituted on the alkyl by $R_{26}$.

The compounds of formula (I') in which $R'_6$ is a carboxyl can be used to obtain the compounds of formula (I) in which $R_6$ is a group —$CONR_{17}R_{18}$ by reaction with a compound of the formula $HNR_{17}R_{18}$, in the presence of BOP and an amine such as diisopropylethylamine.

In the same way, the compounds of formula (I) which $R_6$ is a group —$CONHCR_{10}R_{23}COR_{12}$ are prepared from compounds of formula (I') in which $R'_6$ is either a group —COCl or a phenoxycarbonyl group by reaction with $H_2NCR_{10}R_{23}COR_{12}$. They can also be prepared from compounds of formula (I') in which $R'_6$ is a carboxyl by reaction with a compound $H_2NCR_{10}R_{23}COR_{12}$, in the presence of BOP and an amine such as diisopropylethylamine.

The compounds of formula (I) in which $R_6$ is group —$COR_{25}$ are prepared from corresponding compounds (I') in which $R'_6$ is a phenoxycarbonyl by reaction with $R_{25}H$.

A compound (I) in which $R_6$ is a thiocarbamoyl be prepared by reacting Lawesson's reagent with compound (I) in which $R_6$ is the corresponding carbamoyl.

A compound of formula (I') in which $R'_6$ is nitro group makes it possible to obtain a compound (I) which $R_6$ is an amino group by catalytic hydrogenation, for example in the presence of platinum oxide, Raney® nickel or palladium-on-charcoal, or by chemical reduction, for example in the presence of tin or iron in an acid medium; other compounds in which the amino group is substituted can then be prepared using reactions well known to those skilled in the art.

To prepare compounds of formula (I) in which $R_1$ and/or $R_6$ is a ($C_1$–$C_7$)monoalkylamino, a compound of formula (I') in which $R'_1$ and/or $R'_6$ is an amino group is reacted with an aldehyde or a ketone in an acid medium, in the presence of a reducing agent such as sodium cyanoborohydride; the compounds (I) in which $R_1$ and/or $R_6$ is a dialkylamino are prepared by an identical reaction.

The compounds of formula (I) in which $R_6$ is an amino group substituted by a benzyl, which is itself optionally substituted, or by a $C_3$–$C_8$-alkene can be prepared by reacting a benzyl chloride or a $C_3$–$C_8$-chloroalkene with a compound of formula (I') in which $R'_6$ is an amino or ($C_1$–$C_7$)alkylamino group.

The compounds of formula (I) in which $R_6$ is a Δ3-pyrrolin-1-yl group are prepared by reacting cis-1,4-dichlorobut-2-ene with the compounds of formula (I') in which $R'_6$ is an amino group, in the presence of a base such as triethylamine and under an inert atmosphere. The compounds of formula (I) in which $R_6$ is a pyrrolidin-1-yl group are then prepared by hydrogenation. The reaction of cis-1,4-dichlorobut-2-ene with the compounds (I') in which $R'_6$ is an amino group can also be carried out in air, in the presence of a base such as sodium carbonate, under which conditions it results in the formation of a mixture of a compound of formula (I) in which $R_6$ is a Δ3-pyrrolin-1-yl group and a compound of formula (I) in which $R_6$ is a pyrrol-1-yl group, which can be separated by chromatography.

The compounds of formula (I) in which $R_6$ is an isoindolin-2-yl group are prepared by reacting α,α'-dibromo-o-xylene with the compounds of formula (I') in which $R'_6$ is an amino group, in the presence of a base such as triethylamine, and in a solvent such as dimethylformamide, under reflux.

The compounds of formula (I) in which $R_6$ is a 1-methyl-2,4-dioxoimidazolin-3-yl group ($NR_8R_9$=N-methylhydantoin) are prepared in two steps: Sarcosine is reacted with a compound of formula (I') in which $R'_6$ is a phenoxycarboxamido, in the presence of a base such as triethylamine, to give a compound of formula (I') in which $R'_6$ is an N'-carboxymethyl-N'-methylureido; the previously obtained product then cyclizes on heating at 100° C. under vacuum.

In a similar manner, a compound of formula (I) in which $R_6$ represents a 2,4-dioxoimidazolin-3-yl ($NR_8R_9$hydantoin) may be prepared by reacting glycine with a compound of formula (I') as hereinabove defined.

If $R'_1$ and/or $R'_6$ is an amino, it is also possible to perform a nitrosation, for example in the presence of nitrous acid or sodium nitrite, in order to prepare a compound (I') in which $R'_1$ and/or $R'_6$ is a diazonium salt; the compounds (I) according to the invention in which $R_1$ and/or $R_6$ is a cyano, a halogeno or a $C_1$–$C_7$-alkylthio are then obtained by reactions known to those skilled in the art. Finally, compounds (I) in which $R_1$ and/or $R_6$ is a group of the formula RCONH—, ROCONH—, RNHCONH— or $RSO_2NH$—, in which R is a ($C_1$–$C_7$)alkyl, a group Ar or a group —$CH_2Ar$, can be prepared by conventional reactions starting from compounds (I') in which $R'_1$ and/or $R'_6$=$NH_2$.

The compounds of formula (I) in which $R_6$ is a group —$CH_2NH_2$ are prepared from analogous compounds of formula (I') in which $R'_6$ is a cyano group by the method described in J. Med. Chem., 1990, 33, 2437–2451. These compounds are used to prepare the compounds of formula (I) in which $R_6$ is a group —$CH_2NR_8R_9$, $R_9$ and/or $R_8$ being other than hydrogen, by methods known to those skilled in the art.

The compounds (I) in which $R_6$ is a group —$NR_8R_9$, $R_9$ being a formyl, a ($C_1$–$C_7$)alkylcarbonyl, a ($C_3$–$C_7$) cycloalkylcarbonyl, an optionally substituted benzoyl, a pyridylcarbonyl, a methylpyridylcarbonyl or a thienylcarbonyl, are obtained by reacting the formic acid in the presence of acetic anhydride with a compound (I') in which $R'_6$ is an amino group or respectively by reacting the appropriate anhydride or the appropriate acid chloride with a compound (I') in which $R'_6$ is an amino group, in the presence of an amine such as triethylamine.

In the same way, the acid chloride $R_{11}R_{19}NCR_{10}R_{23}COCl$ is reacted with a compound of formula (I') in which $R'_6$ is an amino group in order to prepare a compound of formula (I) in which $R_6$ is an amino substituted by —$COCR_{10}R_{23}NR_{11}R_{19}$.

To prepare a compound of formula (I) in which $R_6$ is a group —$NR_8CO$—$(C_2-C_7)$alkyl-$NR_{11}R_{19}$, a halogeno $(C_3-C_8)$acyl halide, such as, for example, 3-chloropropionyl chloride or 4-chlorobutyryl chloride, is reacted with a compound of formula (I') in which $R'_6$ is a group —$NHR_8$, in the presence of a base such as triethylamine; the compound obtained is then reacted with an amine $HNR_{11}R_{19}$ to give the compound of formula (I) designated above.

Likewise, a compound of formula (I) in which $R_6$ is a group —$NR_8CO$—$(C_1-C_7)$alkyl-$O$—$CH_2$—$C_6H_5$ is prepared by reacting an ω-benzyloxy-$(C_1-C_7)$alkylcarbonyl halide with a compound of formula (I') in which $R'_6$ is a group —$NHR_8$. Hydrogenation of the previous compound, in the presence of a catalyst such as 5% palladium-on-charcoal, gives a compound of formula (I) in which $R_6$ is a group —$NR_8CO$—$(C_1-C_7)$alkyl-$OH$.

According to another preparatory example, a compound (I) in which $R_6$ is a $(C_1-C_7)$alkylsulfonamido group, a benzylsulfonamido, a group —$NHSO_2Ar$ or a group —$NHSO_2NR_{16}R_{22}$ is obtained by reacting a $(C_1-C_7)$ alkylsulfonyl halide, a benzylsulfonyl halide, a compound $ArSO_2Cl$ or a compound $R_{22}R_{16}NSO_2Cl$, respectively, with a compound (I') in which $R'_6$ is an amino group.

The compounds (I') in which $R'_6$ is an amino group are also useful for the preparation of compounds in which this amino group is substituted by a group —$(CH_2)_r$-$COR_{12}$. In this case, a compound of the formula Hal-$(CH_2)_r$-$COOAlk$, in which Hal is a halogen, for example bromine, and Alk is a $C_1-C_7$-alkyl, is reacted with (I') in the presence of cuprous chloride; if required, the resulting ester is converted to the acid or an amide. A compound (I) in which $R_6$ is a group —$NHCO(CH_2)_2CO_2H$ or —$NHCO(CH_2)_3CO_2H$ can be prepared by reacting an anhydride, such as succinic anhydride or glutaric anhydride, with a compound (I') in which $R'_6$ is an amino. If required, the resulting acid is converted to an ester or an amide.

It is also possible to react ethyloxalyl chloride or respectively a ethylmalonyl chloride with a compound (I') in which $R'_6$ is an amino in order to prepare a compound (I) in which $R_6$ is a group —$NHCOCO_2Et$ or respectively a group —$NHCOCH_2CO_2Et$.

In the same way, the compounds of formula (I) in which $R_6$ is an amino group substituted by a group —$CR_{10}R_{23}COR_{12}$ are prepared by reacting a compound of the formula Hal-$CR_{10}R_{23}COR_{12}$ with the corresponding compounds (I') in which the substituent $R'_6$ is an amino.

A compound (I) in which $R_6$ is an amino group substituted by an alkoxycarbonyl, a phenoxycarbonyl or a benzyloxycarbonyl is prepared by reacting a $C_1-C_7$-alkyl, phenyl or benzyl chloroformate with a compound of formula (I') in which the substituent $R'_6$ is an amino.

Likewise, a compound of formula (I) in which $R_6$ is a phenoxythiocarbonylamino is obtained by reacting a phenoxythiocarbonyl chloride with a compound of formula (I') in which $R'_6$ is an amino group.

A compound of formula (I) in which $R_6$ is a ureido or a thioureido is prepared by reacting ammonia with a compound of formula (I') in which $R'_6$ is an amino group substituted by a phenoxycarbonyl or a phenoxythiocarbonyl; such a compound of formula (I') is reacted with a correctly substituted aniline or a correctly substituted $C_1-C_7$-monoalkylamine or $C_1-C_7$-dialkylamine in order to prepare a compound of formula (I) in which $R_6$ is a correctly substituted N'-phenylureido or a correctly substituted N'-alkylureido or N',N'-dialkylureido in which the alkyl is $C_1-C_7$.

It is also possible to prepare other compounds (I) in which $R_6$ is a ureido (—$NHCONR_{14}R_{24}$) or a thioureido (—$NHCSNR_{14}R_{24}$) by reacting a compound $NHR_{14}R_{24}$ with a compound (I') in which $R'_6$ is a phenoxycarbonylamino or, respectively, phenoxythiocarbonylamino group.

A further possibility is to prepare a compound (I) in which $R_6$ is a ureido (—$NHCONR_{14}R_{24}$) or a thioureido by reacting a carbamoyl chloride ($ClCONR_{14}R_{24}$) or, respectively, a thiocarbamoyl chloride with a compound of formula (I') in which $R'_6$ is an amino group.

It is also possible to prepare a compound (I) in which $R_6$ is a thioureido by reacting Lawesson's reagent with a compound (I') in which $R'_6$ is the corresponding ureido.

The compounds (I) in which $R_6$ is a guanidino group which is unsubstituted or monosubstituted or disubstituted by a $C_1-C_7$-alkyl, a phenyl or a benzyl can be prepared from the compounds (I') in which $R'_6$ is a phenoxyamido group by reaction with cyanamide or a derivative thereof correctly substituted on the nitrogen.

The compounds (I) in which $R_6$ is a guanidino group substituted in the 2-position by a cyano are prepared in two steps: Dimethyl N-cyanodithioiminocarbonate is reacted with a compound (I') in which $R'_6$ is an amino, in a solvent such as n-butanol, under reflux, to give a compound (I') in which $R'_6$ is a group —$NHC(SCH_3)$=$N$—$CN$; reaction of the previous compound with an appropriate amine gives the expected compound (I).

It is also possible to prepare a compound (I) in which $R_6$ is an amino group substituted by a $(C_1-C_7)$alkylcarbamoyl or a phenylcarbamoyl by reacting an alkyl or phenyl isocyanate with a compound (I') in which the substituent $R'_6$ is an amino.

Furthermore, a compound (I) in which $R_6$ is a sulfamoyl group substituted by $R_{20}$ and $R_{21}$ is prepared by reacting a compound —$HNR_{20}R_{21}$ with a compound of formula (I') in which $R'_6$ is a halogenosulfonyl group.

The affinity of the compounds according to the invention for the vasopressin receptors was determined in vitro using the method described in C. J. Lynch et al., J. Biol. Chem., 1985, 260 (5), 2844–2851. This method consists in studying the displacement of tritiated vasopressin bound to the $V_1$ sites of rat liver membranes. The concentrations of the compounds according to the invention which cause a 50% inhibition of the binding of tritiated vasopressin ($IC_{50}$) are low, ranging down to $10^{-7}M$.

The affinity of the compounds (I) according to the invention for the $V_2$ receptors was measured on a bovine kidney membrane preparation by a method adapted from P. Crause et al., Molecular and Cellular Endocrinology, 1982, 28, 529–541, and F. L. Stassen et al., J. Pharmacol. Exp. Ther., 1982, 223, 50–54. The compounds according to the invention inhibit the binding of tritiated arginine vasopressin to the receptors of the membrane preparation. The $IC_{50}$ values of the compounds according to the invention are low, ranging down to $10^{-8}M$.

The antagonistic activity of the compounds according to the invention towards the $V_2$ receptors was demonstrated by the adenylate cyclase activity assay performed by a method adapted from M. Laburthe et al., Molecular Pharmacol., 1986, 29, 23–27. A bovine kidney membrane preparation is used and each product is incubated for 10 minutes at 37° C., either by itself or in the presence of AVP (arginine vasopressin) at a concentration of $3.10^{-8}M$. The cyclic AMP (cyclic adenosine monophosphate) produced is measured by radioimmunoassay. The concentration which causes a 50% inhibition ($IC_{50}$) of the stimulation of adenylate cyclase induced by $3.10^{-8}M$ AVP is determined. The $IC_{50}$ values deter mined are of the order of $10^{-7}M$, ranging down to $10^{-8}M$.

The agonistic or antagonistic activity of the compounds according to the invention, administered orally, towards the vasopressin receptors is evaluated in hyperhydrated rats (OFA, Sprague-Dawley strain) treated with vasopressin. The antagonistic activity of the compounds according to the invention was also evaluated in normally hydrated rats (OFA strain or Sprague-Dawley strain) by the technique described in Br. J. Pharmacol., 1992, 105, 787–791. The diuretic effect was observed for some of the compounds at a dose of 10 mg/kg.

Likewise, the affinity of the compounds (I) according to the invention for the oxytocin receptors was determined in vitro by the displacement of a radioiodinated oxytocin analog bound to the receptors of a gestating rat mammary gland membrane preparation by a technique similar to that described by J. Eland et al. in Eur. J. Pharmacol., 1987, 147, 197–207. The $IC_{50}$ values of the compounds according to the invention reach $10^{-7}$M.

The compounds according to the invention are active after administration by different routes, especially orally.

No signs of toxicity are observed with these compounds at the pharmacologically active doses.

Thus the compounds according to the invention can be used in the treatment or prevention of various vasopressin-dependent or oxytocin-dependent complaints, cardiovascular complaints such as hypertension, pulmonary hypertension, cardiac insufficiency, myocardial infarction or coronary vasospasm, in particular in smokers, unstable angina and PTCA (percutaneous transluminal coronary angioplasty), cardiac ischemia, hemostatic disorders, especially hemophilia, and von Willebrand's syndrome, complaints of the central nervous system, for example migraine, cerebral vasospasm, cerebral hemorrhage, cerebral edemas, depression, anxiety, psychotic states and memory disorders, complaints of the renal system, such as edemas, renal vasospasm, necrosis of the renal cortex, hyponatremia, hypokalemia and Schwartz Bartter's syndrome, complaints of the gastric system, such as gastric vasospasm, hepatocirrhosis, ulcers, the pathology of vomiting, for example nausea, including nausea due to chemotherapy, travel sickness or else the syndrome of inappropriate secretion of antidiuretic hormone (SIADH), diabetes insipidus and enuresis. The compounds according to the invention can also be used in the treatment of disorders of sexual behavior; in women, the compounds according to the invention can be used for treating dysmenorrhea or premature labor. The compounds according to the invention can also be used in the treatment of small cell lung cancer, hyponatremic encephalopathy, Raynaud's disease, pulmonary syndrome and glaucoma and in postoperative treatments, especially after abdominal surgery.

The present invention further relates to pharmaceutical compositions containing an effective dose of a compound according to the invention, or a pharmaceutically acceptable salt, and suitable excipients.

Said excipients are chosen according to the pharmaceutical form and the desired mode of administration.

In the pharmaceutical compositions of the present invention for oral, sublingual, subcutaneous, intramuscular, intravenous, topical, intratracheal, intranasal, transdermal or rectal administration, the active principles of formula (I) above, or their salt where appropriate, can be administered to animals and humans in unit forms of administration, mixed with conventional pharmaceutical carriers, for the prophylaxis or treatment of the above disorders or diseases. The appropriate unit forms of administration include forms for oral administration, such as tablets, gelatin capsules, powders, granules and solutions or suspensions to be taken orally, forms for sublingual, buccal, intratracheal or intranasal administration, forms for subcutaneous, intramuscular or intravenous administration and forms for rectal administration. For topical application, the compounds according to the invention can be used in creams, ointments or lotions.

To obtain the desired prophylactic or therapeutic effect, the dose of active principle can vary between 0.01 and 50 mg per kg of body weight and per day.

Each unit dose can contain from 0.5 to 1000 mg, preferably from 1 to 500 mg, of active ingredients in combination with a pharmaceutical carrier. This unit dose can be administered 1 to 5 times a day so as to administer a daily dosage of 0.5 to 5000 mg, preferably 1 to 2500 mg.

If a solid composition is prepared in the form of tablets, the main active ingredient is mixed with a pharmaceutical vehicle such as gelatin, starch, lactose, magnesium stearate, talc, gum arabic or the like. The tablets can be coated with sucrose, a cellulose derivative or other appropriate substances, or else they can be treated so as to have a sustained or delayed activity and so as to release a predetermined amount of active principle continuously.

A preparation in the form of gelatin capsules is obtained by mixing the active ingredient with a diluent and pouring the resulting mixture into soft or hard gelatin capsules.

A preparation in the form of a syrup or elixir or for administration in the form of drops can contain the active ingredient together with a sweetener, which is preferably calorie-free, methylparaben and propylparaben as antiseptics, a flavoring and an appropriate color.

The water-dispersible powders or granules can contain the active ingredient mixed with dispersants or wetting agents, or suspension agents such as polyvinylpyrrolidone, as well as with sweeteners or taste correctors.

Rectal administration is effected using suppositories, which are prepared with binders melting at the rectal temperature, for example cocoa butter or polyethylene glycols.

Parenteral administration is effected using aqueous suspensions, isotonic saline solutions or sterile and injectable solutions which contain pharmacologically compatible dispersants and/or wetting agents, for example propylene glycol or butylene glycol.

The active principle can also be formulated as microcapsules, if appropriate with one or more carriers or additives.

In addition to the products of formula (I) above or one of the pharmaceutically acceptable salts, the compositions of the present invention can contain other active principles which may be useful in the treatment of the disorders or diseases indicated above.

Thus the present invention further relates to pharmaceutical compositions in which several active principles are present in association, one of them being a compound according to the invention.

Thus, according to the present invention, it is possible to prepare pharmaceutical compositions in which a compound according to the invention is present in association with a compound which acts on the renin-angiotensin system, such as a converting enzyme inhibitor, an angiotensin II antagonist or a renin inhibitor. A compound according to the invention can also be associated for example with a peripheral vasodilator, a calcium inhibitor, a beta-blocker, an alpha-1-blocker or a diuretic. Such compositions will be useful in particular in the treatment of hypertension or heart failure.

It is also possible to associate two compounds according to the invention, namely a specific $V_1$ receptor antagonist with a specific $V_2$ receptor antagonist, or else a specific $V_1$ receptor antagonist with a specific oxytocin antagonist.

These associations will make it possible to reinforce the therapeutic activities of the compounds according to the invention.

Preparation of the 1,3-dihydroindol-2-ones

Preparation 1:

1,3-Dihydro-4,6-dimethyl-3-spirocyclohexaneindol-2-one

This compound is prepared according to Moore and Plant in J. Chem. Soc., 1951, 3475.

A mixture containing 15 ml of quinoline and 10 g of calcium oxide is refluxed under an inert atmosphere and 5 g of the 3,5-dimethylphenylhydrazide of cyclohexanecarboxylic acid (IV, $R'_1$, $R'_2$=$CH_3$, $CR_3R_4$=cyclohexane) are added over 30 minutes. The reaction medium is cooled and then poured into an ice/hydrochloric acid mixture. Extraction is carried out with ethyl acetate and the extract is washed with 1N hydrochloric acid and with water until the washings are neutral, and then dried over $Na_2SO_4$ and concentrated under vacuum to give a brown solid. Trituration in iso ether gives the expected compound. M.p.=223° C.

The 1,3-dihydroindol-2-one derivatives described in Table 1 below are obtained by following the same procedure and varying the starting hydrazide.

These compounds are purified by chromatography on a silica column using DCM as the eluent or by chromatography on an alumina column using DCM or iso ether as the eluent.

TABLE 1

| $R'_1$ | $R'_2$ | $CR_3R_4$ | M.p. °C. |
|---|---|---|---|
| 5-Cl | H | cyclobutane | 191 |
| 5-Cl | H | cyclopentane | 189 |
| 5-Cl | H | cyclohexane | 186 |
| H | H | cyclohexane | 123–124 |
| 5-$CH_3$ | H | cyclohexane | 164 |
| 5-$CH_3O$ | H | cyclohexane | 226 |
| 6-Cl | H | cyclohexane | 168 |
| 5-$CF_3O$ | H | cyclohexane | 164 |
| 5-$C_6H_5O$ | H | cyclohexane | 160 |

Preparation 2:

The 1,3-dihydro-3-spirocyclohexaneindol-2-one described in Table 1 above can also be obtained by alkylation of the indol-2-one using the process according to A. S. Kende and J. C. Hodges or a variant described below.

A solution of 30 g of 1,3-dihydroindol-2-one in 900 ml of THF is kept at −40° C. under a nitrogen atmosphere and 101 g of potassium tert-butylate are added. The temperature is allowed to rise to 0° C. over 1 hour, the mixture is then cooled to −60° C. and a solution of 52 g of 1,5-dibromopentane in 50 ml of THF is added dropwise. After 30 minutes at −60° C., the temperature is allowed to rise to RT, 30 ml of water are then added and the solvent is evaporated off under reduced pressure. The residue is taken up with 500 ml of DCM and 200 ml of water, the insoluble material is then filtered off and the organic phase is separated off, washed with 100 ml of water, dried over magnesium sulfate and evaporated under vacuum. The residue is chromatographed on silica using a cyclohexane/ether mixture as the eluent to give the expected compound, which is recrystallized from heptane. m=34 g. M.p.=123°–124° C.

A similar procedure can be applied starting from other 1,3-dihydroindol-2-ones and other alkylating agents.

By way of example, among the starting compounds of formula (VII), 5-chloro-1,3-dihydroindol-2-one is described by Wright in J. Am. Chem. Soc., 1956, 78, 221, and by RajanBabu in J. Org. Chem., 1986, 51, 1704. 4-Chloro-1,3-dihydroindol-2-one can be prepared from 2-chloro-6-nitrotoluene by the method described in J. Am. Chem. Soc., 1956, 78, 221.

1,3-Dihydro-5-methoxyindol-2-one is prepared from 4-methoxyaniline by the method described in J. Am. Chem. Soc., 1974, 96, 5512. In the same way, various 1,3-dihydroindol-2-ones are prepared from the appropriate aniline derivative.

Preparation 3:

5-Ethoxy-1,3-dihydroindol-2-one

A—3-Methylthio-5-ethoxy-1,3-dihydroindol-2-one 23.6 g of ethyl methylthioacetate in 60 ml of DCM are added to a solution, cooled to about −70° C., of 12.5 g of chlorine in 400 ml of DCM. After stirring for 5 minutes at the same temperature, a solution of 4-ethoxyaniline (48.3 g) in 120 ml of DCM is added. The mixture is stirred for one hour at about −70° C., 39.3 ml of triethylamine are added and the resulting mixture is allowed to warm up to room temperature. 200 ml of water are added and the organic phase is decanted, dried over magnesium sulfate and evaporated under reduced pressure. The residue is taken up with 500 ml of isopropanol and 20 ml of concentrated hydrochloric acid. The mixture is stirred for about 16 hours at room temperature and filtered and the precipitate is separated off. The filtrate is concentrated under reduced pressure to give the expected product.

B—5-Ethoxy-1,3-dihydroindol-2-one

The above solid, in 1500 ml of isopropanol, is dethiomethylated in the presence of 100 g of Raney® nickel (80 to 100 m² per g), under reflux, for 3 hours, under a nitrogen atmosphere. The mixture is filtered on talc, the material on the filter is rinsed with 1000 ml of isopropanol and the filtrate is concentrated under reduced pressure. 16 g of the expected product are isolated after recrystallization from toluene. M.p.=156° C.

The following are isolated in the same manner starting from the corresponding anilines:

| | |
|---|---|
| 5-benzyloxy-1,3-dihydroindol-2-one | m.p. = 152° C. |
| 5-n-propyl-1,3-dihydroindol-2-one | m.p. = 136° C. |
| 5-ethyl-1,3-dihydroindol-2-one | m.p. = 152° C. |
| 5-(2,2,2-trifluoroethoxy)-1,3-dihydroindol-2-one | m.p. = 145° C. |
| 5-trifluoromethyl-1,3-dihydroindol-2-one | m.p. = 193° C. |
| 5-fluoro-1,3-dihydroindol-2-one | m.p. = 143° C. |

The compounds of formula (II) described below are obtained by following the technique described in Preparation 2 and varying the starting 1,3-dihydroindol-2-one derivative and the alkylating reagent.

TABLE 2

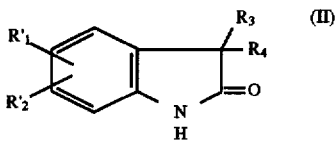

| R'₁ | R'₂ | CR₃R₄ | M.p. °C. | Alkylating reagent |
|---|---|---|---|---|
| 5-Cl | H | cyclohexane | 186–189 | Br(CH₂)₅Br |
| 5-Cl | H | cycloheptane | 202 | Br(CH₂)₆Br |
| 5-Cl | H | 4,4-dimethylcyclohexane | 180 | TsO(CH₂)₂C(CH₃)₂—(CH₂)₂OTs |
| 5-Cl | H | 2-hexahydroindane | 223 | 1,2-cis-diiodomethyl-cyclohexane |
| 5-CH₃O | H | 4,4-dimethylcyclohexane | 202 | TsO(CH₂)₂C(CH₃)₂—(CH₂)₂—OTs |
| 5-Cl | H | 2-indane | 228 | α,α'-dibromomethyl-orthoxylene |
| 5-Cl | H | N-methyl-4-piperidine | 260 | Cl(CH₂)₂N(CH₃)—(CH₂)₂Cl |
| 5-Cl | H | 4-tetrahydropyran | 223 | I(CH₂)₂O(CH₂)₂I |
| 4-Cl | H | cyclohexane | 215 | Br(CH₂)₅Br |
| 5-BzO | H | cyclohexane | 162 | Br(CH₂)₅Br |
| 5-Cl | H | 2,3-dihydro-2-phenalene | — | 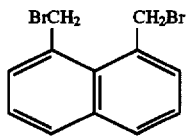 |
| 5-BzO | H | 4,4-dimethylcyclohexane | 154 | TsO(CH₂)₂C(CH₃)₂—(CH₂)₂OTs |
| 5-Cl | H | 4-spirocyclopentane | 202 | 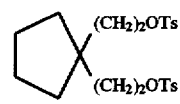 |
| 5-nPr | H | cyclohexane | 151 | Br(CH₂)₅Br |
| 5-EtO | H | N-tBu-4-piperidine | — | 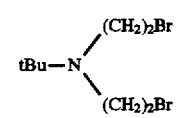 |
| 5-Cl | H | N-Bz-4-piperidine | 165 | 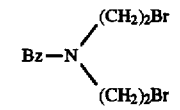 |
| 5-Cl | H | N-phenyl-4-piperidine | 188 | 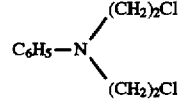 |
| 5-Cl | H | 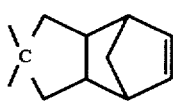 | 300 | 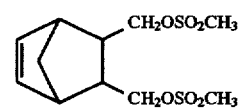 |
| 5-EtO | H | 4,4-diethylcyclohexane | 132 | TsO(CH₂)₂C(C₂H₅)₂—(CH₂)₂OTs |
| 5-EtO | H | cyclohexane | 163 | Br(CH₂)₅Br |
| 5-EtO | H | 4,4-dimethylcyclohexane | 178 | TsO(CH₂)₂C(CH₃)₂—(CH₂)₂OTs |
| 5-EtO | H | cycloheptane | 139 | Br(CH₂)₆Br |
| 5-Et | H | 4,4-dimethylcyclohexane | 160 | TsO(CH₂)₂C(CH₃)₂—(CH₂)₂OTs |
| 5-CF₃CH₂O | H | 4,4-dimethylcyclohexane | 164 | TsO(CH₂)₂C(CH₃)₂—(CH₂)₂OTs |
| H | H | 4,4-dimethylcyclohexane | 169 | TsO(CH₂)₂C(CH₃)₂—(CH₂)₂OTs |
| 5-CF₃ | H | 4,4-dimethylcyclohexane | 211 | TsO(CH₂)₂C(CH₃)₂—(CH₂)₂OTs |

TABLE 2-continued

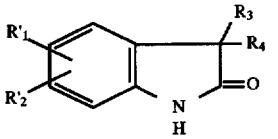

(II)

| R'₁ | R'₂ | CR₃R₄ | M.p. °C. | Alkylating reagent |
|---|---|---|---|---|
| 5-F | H | 4,4-dimethylcyclohexane | 171 | TsO(CH₂)₂C(CH₃)₂—(CH₂)₂OTs |
| 5-Cl | H | 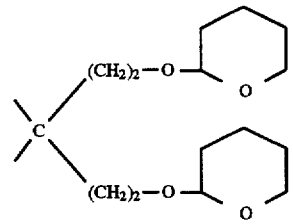 | 120 | Br(CH₂)₂—O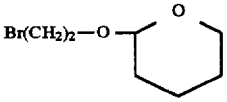 |
| 5-EtO | H | 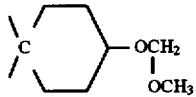 | NMR (1) | TsO(CH₂)₂—CH—(CH₂)₂OTs<br>             OCH₂OCH₃ |
| 5-EtO | H | 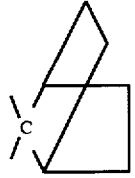 | 208 | 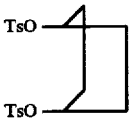 |
| 5-EtO | H | 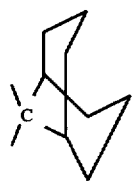 | 214 | 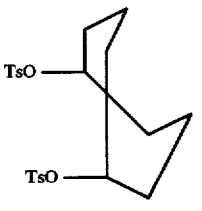 |
| 5-EtO | H | 4-tetrahydropyrane | 146 | I(CH₂)₂O(CH₂)₂I |
| 5-EtO | H | 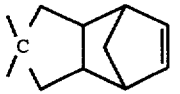 | 255 | 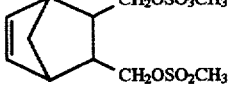 |

(1) NMR at 200 MHz in CDCl₃:
8.3 ppm: s: 1H
7.1 ppm: d: 1H
6.7 ppm: m: 2H
4.7 ppm: s: 2H
3.9 ppm: q: 2H
3.8 ppm: m: 1H
3.4 ppm: s: 3H
2.2 ppm: m: 2H
1.8 ppm: m: 6H
1.4 ppm: t: 3H Preparation 4:
1,3-Dihydro-3-spiroadamantaneindol-2-one
This compound is prepared according to I. Fleming et al., Tetrahedron Letters, 1982, 2053–2056, starting from 2-bromoaniline and adamantan-2-one.

Preparation 5:
1,3-Dihydro-5-nitro-3-spirocyclohexaneindol-2-one
This compound is prepared by the method described in J. Am. Chem. Soc., 1945, 67, 499, by the nitration of 1,3-dihydro-3-spirocyclohexaneindol-2-one. M.p.=192° C.

1,3-Dihydro-5-nitro-3-spiroadamantaneindol-2-one is prepared in the same manner starting from 1,3-dihydro-3-spiroadamantaneindol-2-one. M.p.>260° C.

1,3-Dihydro-5-nitro-3-spiro(4,4-dimethylcyclohexane)indol-2-one is also prepared. M.p.=195° C.

Preparation 6:
5-Amino-1,3-dihydro-3-spirocyclohexaneindol-2-one
This compound is prepared by the method described in J. Chem. Soc., 1951, 3475, by the reduction of 1,3-dihydro-5-nitro-3-spirocyclohexaneindol-2-one, prepared above. M.p.=176° C.

5-Amino-1,3-dihydro-3-spiroadamantaneindol-2-one is prepared in the same manner. M.p.=245° C.

Preparation 7:

5-Fluoro-1,3-dihydro-3-spirocyclohexaneindol-2-one

A—5-Diazonium-1,3-dihydro-3-spirocyclohexaneindol-2-one tetrafluoroborate

A solution containing 4 g of 5-amino-1,3-dihydro-3-spirocyclohexaneindol-2-one in 9.2 ml of 6N hydrochloric acid is cooled to 0° C. and 2.27 g of sodium nitrite in 2.6 ml of water are added, followed by 2.54 g of sodium tetrafluoroborate in 9 ml of water. After stirring for 5 minutes, the precipitate is filtered off and washed with a 5% solution of tetrafluoroborate, with 3 ml of methanol cooled to about 0° C. and then with 5 ml of ether. The salt obtained is dried under vacuum at RT in the presence of phosphorus pentoxide.

B—5-Fluoro-1,3-dihydro-3-spirocyclohexaneindol-2-one 1 g of the compound obtained in step A is placed in 5 ml of xylene and heated at about 115° C. for 2 hours. The mixture is cooled to RT, the precipitate is filtered off and rinsed with toluene and 0.1 g of active charcoal is added to the filtrate. After filtration, the solvent is evaporated off under reduced pressure to give 0.45 g of the expected compound, which is recrystallized from pentane. M.p.=114° C.

Preparation 8:

5-Cyano-1,3-dihydro-3-spirocyclohexaneindol-2-one 4.78 g of potassium cyanide and 4.95 g of cuprous cyanide are dissolved at RT in 40 ml of DMSO. The solution is cooled to about 15° C. and 4.15 g of the diazonium salt obtained in step A of the previous preparation are added.

After stirring for 30 minutes at RT, 100 ml of water and 100 ml of ether are added and the organic phase is then separated off, dried over magnesium sulfate and evaporated under reduced pressure. The residue is chromatographed on silica using a cyclohexane/ether mixture as the eluent to give the expected compound, which is recrystallized from heptane. m=1.4 g. M.p.=216° C.

Preparation 9:

5-Chloro-1,3-dihydro-3-spiroadamantaneindol-2-one 1 g of the p-chlorophenylhydrazide of adamantane-2-carboxylic acid is dissolved in THF and 2.5 ml of a solution of n-butyllithium (1.6M in hexane) are added at −40° C. After stirring for 5 minutes, the mixture is concentrated under vacuum, the temperature being kept below 30° C. 30 ml of 1,2,3,4-tetramethylbenzene are added and the mixture is refluxed for 1 hour. It is concentrated under reduced pressure, the residue is taken up with normal hydrochloric acid, extraction is carried out with ether and the extract is washed, dried and concentrated under vacuum. The oil obtained is chromatographed on a silica column using DCM as the eluent to give 0.3 g of the expected product in the form of a wax, which is crystallized from iso ether. M.p.=249° C.

Preparation 10:

5-Acetyl-1,3-dihydro-3-spirocyclohexaneindol-2-one 2.56 g of acetyl chloride and then 8.25 g of anhydrous aluminum chloride are added to a solution, cooled to 5° C., of 4 g of 1,3-dihydro-3-spirocyclohexaneindol-2-one in 35 ml of 1,2-dichloroethane. The mixture is refluxed for 2 hours, the solvent is evaporated off under reduced pressure and the medium is hydrolyzed with 50 g of ice and extracted with ethyl acetate.

The organic phase is washed with water, dried over magnesium sulfate and then evaporated under reduced pressure. The residue is chromatographed on a silica column using a mixture of heptane and ethyl ether as the eluent to give 3.6 g of the expected product. M.p.=192° C.

Preparation 11:

5-Chloro-1,3-dihydro-3-spiro(4-tetrahydrothiopyran)indol-2-one

A—5-Chloro-1,3-dihydro-3,3-di(2-bromoethyl)-indol-2-one 7.66 g of bromine are added slowly to a mixture, cooled to about 0° C., of 12.4 g of triphenylphosphine in 70 ml of DCM, and 4.58 g of 5-chloro-1,3- dihydro-3,3-di[2-(tetrahydropyran-2-yloxy)ethyl]indol-2-one, described in Table 2, are then added. After 16 hours at RT, 60 ml of water are added and the organic phase is separated off, washed with 60 ml of water and then dried over magnesium sulfate and evaporated under vacuum. The residue is chromatographed on a silica column using DCM as the eluent to give 3.12 g of the expected product. M.p.=215° C.

B—5-Chloro-1,3-dihydro-3-spiro(4-tetrahydrothiopyran)indol-2-one

Under an inert atmosphere, 3 g of the product prepared in step A are added to 3.2 ml of DMF and 2 g of sodium sulfide monohydrate and the mixture is heated for 2 hours at 50° C. It is cooled to RT, 6 ml of water are added and the mixture is extracted with DCM. The organic phase is washed with water, dried over magnesium sulfate and evaporated under reduced pressure. The oily residue obtained is purified by chromatography on silica using DCM as the eluent to give 2.02 g of the expected compound.

NMR spectrum at 200 MHz in $CDCl_3$:

8.12 ppm: s: 1H 7.2 ppm: m: 2H 6.8 ppm: d: 1H 3.25 ppm: m: 2H 2.65 ppm: m: 2H 2 ppm: m: 4H Preparation 12:

5-Ethoxy-1,3-dihydro-3-spiro[4-tricyclo-[$5.2.1.0^{2,6}$] decane]indol-2-one

A mixture of 3 g of 5-ethoxy-1,3-dihydro-3-spiro[4-tricyclo[$5.2.1.0^{2,6}$]dec-8-ene]indol-2-one, described in Table 2, and 1.5 g of 5% palladium-on-charcoal in 160 ml of MeOH is hydrogenated for 16 hours at 40° C. under a pressure of 20 bar. The catalyst is filtered off on CéliteR and washed with MeOH and the filtrate is evaporated under vacuum to give 2.95 g of the expected product. M.p.=236° C.

Preparations 13 and 14:

5-Ethoxy-1,3-dihydro-3-spiro(4-methoxycyclohexane) indol-2-one, isomer A and isomer B A) 3-Methoxypentane-1,5-diol 25 ml of methyl trifluoromethylsulfonate are added to a solution of 30 g of diethyl 3-hydroxyglutarate and 33 ml of 2,6-di-tert-butylpyridine in 500 ml of DCM and the mixture is refluxed for 5 hours. After cooling, 500 ml of a 0.5N solution of HCl are added, the organic phase is decanted and dried over magnesium sulfate and the solvent is evaporated off under vacuum. The solid obtained is taken up with 200 ml of anhydrous THF, the mixture is filtered and the filtrate is then cooled to −5° C. 160 ml of a 1M solution of lithium aluminum hydride in THF are then added slowly and the mixture is stirred for 16 hours, the temperature being allowed to rise to RT. The reaction mixture is cooled to 0° C. and 5.5 ml of water, 18 ml of a 15% solution of NaOH and 5.5 ml of water are added successively. The mineral salts are filtered off and the filtrate is evaporated under vacuum to give the expected product after distillation under reduced pressure. B.p.=104° C. under 1.5 Pa.

B) 3-Methoxy-1,5-ditosyloxypentane

A solution of 31 g of p-toluenesulfonyl chloride and 26 ml of triethylamine in 120 ml of THF is cooled to 0° C., 10 g of the compound obtained in the previous step are added and the mixture is stirred for 24 hours at RT. 120 ml of water are added to the reaction mixture, the solvent is evaporated off under vacuum, the residue is extracted with AcOEt and dried over magnesium sulfate and the solvent is evaporated off under vacuum. The oil obtained is taken up with 200 ml of ether and 200 ml of 2N NaOH and the mixture is stirred for 16 hours at RT. After decantation, the organic phase is dried over magnesium sulfate and the solvent is evaporated off under vacuum to give 26 g of the expected product after crystallization from cyclohexane. M.p.=58° C.

C) 5-Ethoxy-1,3-dihydro-3-spiro(4-methoxycyclohexane)indol-2-one, isomer A and isomer B These compounds are prepared by the procedure described in Preparation 2 starting from 11.85 g of 5-ethoxy-1,3-dihydroindol-2-one, 34 g of potassium tert-butylate and 26 g of the compound obtained in the previous step. They are chromatographed on silica using a cyclohexane/AcOEt mixture (80/20; v/v) as the eluent. The two isomers are separated into the less polar isomer, A: compound of Preparation 13, m.p.=173° C.;

the more polar isomer, B: compound of Preparation 14, m.p.=186° C.

EXAMPLE 1

5-Chloro-1,3-dihydro-1-(3,4-dimethoxybenzyl)-3-spirocyclopentaneindol-2-one 66 mg of sodium hydride as an 80% dispersion in oil are added in portions to a solution of 440 mg of 5-chloro-1,3-dihydro-3-spirocyclopentaneindol-2-one in 5 ml of DMF; after stirring for 30 minutes, 510 mg of 1-bromomethyl-3,4-dimethoxybenzene are introduced and the mixture is then stirred for 24 hours at RT. The solvent is evaporated off under vacuum and the residue is then extracted with ethyl acetate, washed with water and dried over sodium sulfate. After evaporation of the solvents, the residue is chromatographed on silica using a DCM/AcOEt mixture (97/3; v/v) as the eluent to give 250 mg of the expected product.

NMR spectrum at 200 MHz in DMSO:

1.7–2.1 ppm: m: 8H 3.7 ppm: s: 6H 4.8 ppm: s: 2H 6.7 ppm: d of d: 1H 6.9 ppm: m: 3H 7.2 ppm: d of d: 1H 7.4 ppm: d: 1H

EXAMPLE 2

1,3-Dihydro-1-(2,4-dimethoxybenzyl)-3-spiro(N-methylpiperidine-4)indol-2-one

A solution of 2.08 g of 1-hydroxymethyl-2,4-dimethoxybenzene in 20 ml of ether is cooled to −10° C. under nitrogen and a solution of 0.4 ml of phosphorus tribromide in 8 ml of ether is added dropwise; the resulting 1-bromomethyl-2,4-dimethoxybenzene is kept at −30° C.

A solution of 1.78 g of 1,3-dihydro-3-spiro(N-methylpiperidine-4)indol-2-one in 170 ml of THF is cooled to −50° C. under nitrogen, 0.970 g of potassium tert-butylate is added and the temperature is allowed to rise to 0° C.; the mixture is cooled again to −50° C. and a further 1.380 g of potassium tert-butylate are added. After cooling to −70° C., the brominated derivative prepared above is added and the temperature is then allowed to rise to RT. 20 ml of water are added, the solvents are concentrated under vacuum, the residue is extracted with AcOEt and dried over sodium sulfate and the solvent is evaporated off. The residue is chromatographed on silica using a DCM/MeOH mixture (9/1; v/v) as the eluent. The expected product crystallizes from pentane. m=1.260 g. M.p.=101° C.

EXAMPLE 3

1,3-Dihydro-1-(2,4-dimethoxybenzyl)-3-spiro(N-ethoxycarbonylpiperidine-4)indol-2-one A solution of 1.152 g of ethyl chloroformate in 1.5 ml of benzene is brought to the reflux point and a solution of 1.3 g of the compound obtained in the previous Example in 10 ml of benzene is added dropwise. After refluxing for 6 hours, the solvent is evaporated off under vacuum and the residue is taken up with water. It is extracted with ethyl acetate and washed with a 2N solution of hydrochloric acid and then with water. The expected product crystallizes from iso ether. m=1.12 g. M.p.=156° C.

EXAMPLE 4

5-Chloro-1,3-dihydro-1-(3,5-dimethoxybenzyl)-3-spirocyclohexaneindol-2-one 0.03 g of sodium hydride as an 80% dispersion in oil is added in portions to a solution of 0.236 g of 5-chloro-1,3-dihydro-3-spirocyclohexaneindol-2-one in 5 ml of THF and the mixture is stirred for 30 minutes. It is cooled in an ice bath, 0.190 g of 1-chloromethyl-3,5-dimethoxybenzene is added slowly and the temperature is then allowed to rise to RT. After refluxing for 5 hours, the solvent is evaporated off under vacuum and the residue is taken up with water. It is extracted with ether, washed with water and dried over sodium sulfate, the solvents are evaporated off and the residue is then chromatographed on silica using DCM/AcOEt (99/1; v/v) as the eluent. The expected product crystallizes from iso ether. m=0.044 g. M.p.=106° C.

EXAMPLE 5

Methyl 4-(5-ethoxy-2,3-dihydro-2-oxo-3-spirocyclohexaneindol-1-yl)methyl-3-methoxybenzoate 0.33 g of sodium hydride as an 80% dispersion in oil is added to a solution of 5-ethoxy-1,3-dihydro-3-spirocyclohexaneindol-2-one in 20 ml of DMF, after which 2.85 g of methyl 4-bromomethyl-3-methoxybenzoate are introduced. After stirring for 4 hours at RT, the solvent is evaporated off and the residue is taken up with water. It is extracted with DCM, washed with water and dried over sodium sulfate, the solvents are evaporated off and the residue is then chromatographed on silica using a DCM/AcOEt mixture (97.5/2.5; v/v) as the eluent. The expected product crystallizes from heptane.

m=3.445 g. M.p.=142° C.

EXAMPLE 6

4-(5-Ethoxy-2,3-dihydro-2-oxo-3-spirocyclohexaneindol-1-yl)methyl-3-methoxybenzoic acid A solution containing 847 mg of the compound prepared in the previous Example and 420 mg of lithium hydroxide monohydrate in 9 ml of MeOH, 9 ml of THF and 3 ml of water is stirred for 4 hours at RT. It is diluted with water, acidified to pH 1 by the addition of 1N hydrochloric acid, extracted with DCM, washed with water and dried over sodium sulfate. After evaporation of the solvent, the expected product crystallizes from ether. m=745 mg. M.p.= 215°–217° C.

EXAMPLE 7

5-Ethoxy-1,3-dihydro-1-[2-methoxy-4-[N-(2-methylphenyl)carbamoyl]benzyl]-3-spirocyclohexaneindol-2-one A) 4-(5-Ethoxy-2,3-dihydro-2-oxo-3-spirocyclohexaneindol-1-yl)methyl-3-methoxybenzoyl chloride A solution of 2.1 g of the acid prepared in the previous Example in 20 ml of thionyl chloride is refluxed for 2 hours. It is evaporated under vacuum and the residue is taken up with toluene and then concentrated. The oily residue obtained is used as such in the next step.

B) 5-Ethoxy-,1,3-dihydro-1-[2-methoxy-4-[N-(2-methylphenyl)carbamoyl]benzyl]-3-spirocyclohexaneindol-2-one A solution containing 860 mg of the acid chloride prepared in the previous step, 0.2 ml of 2-methylaniline and 2 ml of TEA in 80 ml of DCM is stirred for 24 hours at RT. It is washed successively with water, with 1N HCl, with water, with a saturated solution of $NaHCO_3$ and then with water. After drying over sodium sulfate and evaporation of the solvents, the residue is chromatographed on silica using DCM/acetone (98/2; v/v) as the eluent. The expected product crystallizes from MeOH. m=0.082 g. M.p.=168° C.

EXAMPLE 8

5-Ethoxy-1,3-dihydro-1-(2-methoxy-4-nitrobenzyl)-3-spirocyclohexaneindol-2-one 0.66 g of sodium hydride as an 80% dispersion in oil is added in portions to a solution of 4.9 g of 5-ethoxy-1,3-dihydro-3-spirocyclohexaneindol-2-one in 40 ml of DMF. After stirring for 15 minutes, 5.4 g of 1-bromomethyl-2-methoxy-4-nitrobenzene are introduced and the mixture is stirred for 24 hours at RT. The solvent is evaporated off under vacuum and the residue is then taken up with water, extracted with DCM, washed with water and dried over sodium sulfate. After evaporation of the solvent, the residue is chromatographed on silica using DCM/AcOEt (98/2; v/v) as the eluent to give the expected product, which is taken up with MeOH and filtered off. m=6.7 g. M.p.=170° C.

EXAMPLE 9

5-Ethoxy-1,3-dihydro-1-(2-methoxy-4-aminobenzyl)-3-spirocyclohexaneindol-2-one

A mixture of 6.157 g of the compound prepared in the previous Example and a few grams of Raney® nickel in 270 ml of 95° ethanol is hydrogenated for 24 hours at RT under a pressure of 50 bar. The reaction medium is filtered on Célite®, the material on the filter is washed with DCM and the solvents are then evaporated off under vacuum. The expected product crystallizes from MeOH. m=4.1 g. M.p.= 81° C.

EXAMPLE 10

5-Ethoxy-1,3-dihydro-1-[4-(Δ3-pyrrolin-1-yl)-2-methoxybenzyl]-3-spirocyclohexaneindol-2-one 1.52 g of the compound prepared in the previous Example, 1.05 g of cis-1,4-dichlorobut-2-ene and 1.74 ml of TEA are mixed with 35 ml of DMF and the mixture is refluxed for 30 minutes. The solvent is evaporated off under vacuum and the residue is taken up with water and then extracted with AcOEt, washed with water and dried over sodium sulfate. After evaporation of the solvent, the residue is chromatographed on silica using DCM/MeOH (98/2; v/v) as the eluent. The expected compound crystallizes from iso ether. m=0.835 g. M.p.=114° C.

EXAMPLE 11

1-(4-Dimethylamino-2-methoxybenzyl)-5-ethoxy-1,3-dihydro-3-spirocyclohexaneindol-2-one 420 mg of the compound prepared in Example 9 and 4 ml of 37% formaldehyde are mixed with 10 ml of acetonitrile; 0.5 g of sodium cyanoborohydride and 0.15 ml of AcOH are added and the mixture is then stirred for 48 hours. After evaporation of the solvent, the residue is taken up with water and then extracted with AcOEt and dried over sodium sulfate. The solvent is evaporated off and the residue is then chromatographed on silica using DCM/AcOEt (90/10; v/v) as the eluent. The expected compound crystallizes from heptane. m=0.29 g. M.p.=138° C.

EXAMPLE 12

5-Ethoxy-1-[4-(2-ethylbutyroylamino)-2-methoxybenzyl]-1,3-dihydro-3-spirocyclohexaneindol-2-one 420 mg of the compound prepared in Example 9 and 1.65 ml of TEA are placed in 20 ml of DCM, 0.5 g of 2-ethylbutyroyl chloride is added slowly and the mixture is stirred for 2 hours at RT. The organic phase is washed with water, dried over sodium sulfate and evaporated under vacuum. The residue is chromatographed on silica using DCM/MeOH (99/1; v/v) as the eluent. The expected product crystallizes from a pentane/iso ether mixture. m=0.30 g. M.p.=119° C.

EXAMPLE 13

1-(4-Diethylaminoacetylamino-2-methoxybenzyl)-5-ethoxy-1,3-dihydro-3-spirocyclohexaneindol-2-one A) 1-(4-Chloroacetylamino-2-methoxybenzyl)-5-ethoxy-1,3-dihydro-3-spirocyclohexaneindol-2-one A solution of 420 mg of the compound prepared in Example 9 and 1 ml of TEA in 12.5 ml of DCM is prepared, 0.27 ml of chloroacetyl chloride is added and the mixture is stirred for 2 hours. After washing with water, it is dried over sodium sulfate, the solvents are evaporated off and the residue is then chromatographed on silica using DCM/MeOH (98/2; v/v) as the eluent. The expected product crystallizes from iso ether. m=0.36 g. M.p.=204° C.

B) 1-(4-Diethylaminoacetylamino-2-methoxybenzyl)-5-ethoxy-1,3-dihydro-3-spirocyclohexaneindol-2-one A solution containing 340 mg of the compound prepared in the previous step and 7 ml of diethylamine in 15 ml of THF is stirred for 48 hours at RT. The solvent is evaporated off under vacuum and the residue is then chromatographed on silica using DCM/MeOH (98/2; v/v) as the eluent. The expected product crystallizes from a pentane/iso ether mixture. m=0.165 g. M.p.=75° C.

EXAMPLE 14

5-Ethoxy-1,3-dihydro-1-[2-methoxy-4-(orthomethylbenzamido)benzyl]-3-spirocyclohexaneindol-2-one A solution containing 285 mg of the compound prepared in Example 9, 0.1 ml of ortho-methylbenzoyl chloride and 0.75 mg of TEA in 30 ml of DCM is stirred for 24 hours at RT. It is washed with water and dried over sodium sulfate, the solvent is evaporated off and the residue is then chromatographed on silica using DCM/MeOH (99.5/0.5; v/v) as the eluent. The expected product crystallizes from iso ether. m=285 mg. M.p.=158° C.

EXAMPLE 15

5-Chloro-1,3-dihydro-1-(2-methoxy-4-nitrobenzyl)-3-spirocyclohexaneindol-2-one 0.528 g of sodium hydride as an 80% dispersion in oil is added in portions to a solution of 4.434 g of 5-chloro-1,3-dihydro-3-spirocyclohexaneindol-2-one in 40 ml of DMF. The mixture is cooled in an ice bath, 5.4 g of 1-bromomethyl-2-methoxy-4-nitrobenzene are then added slowly and the mixture is stirred for 24 hours at RT. It is extracted with ether, washed with water and dried over sodium sulfate and the solvent is then concentrated. The residue is chromatographed on silica using DCM as the eluent. The expected product crystallizes from methanol. m=6.13 g. M.p.=180° C.

EXAMPLE 16

1-(4-Amino-2-methoxybenzyl)-5-chloro-1,3-dihydro-3-spirocyclohexaneindol-2-one

A mixture of 5.8 g of the compound prepared in the previous Example and a few grams of Raney® nickel in 250 ml of 95° ethanol is hydrogenated for 24 hours at RT under a pressure of 50 bar. The catalyst is filtered off on Célite® and the filtrate is then evaporated under vacuum. The expected product crystallizes from methanol. m=3.25 g. M.p.=88° C.

EXAMPLE 17

5-Chloro-1,3-dihydro-1-(4-phenoxycarbonylamino-2-methoxybenzyl)-3-spirocyclohexaneindol-2-one 740 mg of the compound prepared in the previous Example are placed in 25 ml of THF, 210 mg of sodium hydroxide in 1.7 ml of water are added, the mixture is cooled to about 5°–10° C. and 0.9 ml of phenyl chloroformate in 25 ml of THF is then added dropwise. The mixture is stirred for 2 hours at RT. The solvent is evaporated off and the residue is taken up with water and then extracted with ether and washed with water. After drying over sodium sulfate and evaporation of the solvent, the residue is chromatographed on silica using a DCM/MeOH mixture (98/2; v/v) as the eluent. The expected product crystallizes from ethanol. m=0.63 g. M.p.=196° C.

EXAMPLE 18

5-Chloro-1,3-dihydro-1-[2-methoxy-4-(N'-methylureido)benzyl]-3-spirocyclohexaneindol-2-one A solution of 0.30 g of the compound prepared in Example 16 in 20 ml of DCM is cooled to 0° C. and 0.05 ml of methyl isocyanate is added. After stirring for 24 hours at RT, the mixture is washed with water, dried over sodium sulfate and evaporated under vacuum. The residue is chromatographed on silica using DCM/MeOH (98/2; v/v) as the eluent. The expected compound crystallizes from iso ether. m=0.280 g. M.p.=230° C.

EXAMPLE 19

5-Chloro-1,3-dihydro-1-[4-(3,4-dimethoxybenzenesulfonylamino)-2-methoxybenzyl]-3-spirocyclohexaneindol-2-one 200 mg of 3,4-dimethoxybenzenesulfonyl chloride are added to a solution of 280 mg of the compound prepared in Example 16 in 10 ml of pyridine and the mixture is stirred for 24 hours at RT. The solvent is evaporated off under vacuum and the residue is then taken up with water. It is extracted with DCM, washed with 1N hydrochloric acid and then with water, dried over sodium sulfate and evaporated under vacuum. The expected compound crystallizes from ethanol. m=0.31 g. M.p.=180° C. EXAMPLE 20

5-Chloro-1,3-dihydro-1-(4-dimethylaminosulfonamido-2-methoxybenzyl)-3-spirocyclohexaneindol-2-one A solution containing 371 mg of the compound prepared in Example 16 and 0.12 ml of dimethylaminosulfamoyl chloride in 10 ml of pyridine is stirred for 72 hours. The solvent is evaporated off and the residue is taken up with water and then extracted with ether and washed with 1N hydrochloric acid and with water. After drying over sodium sulfate and evaporation of the solvent, the residue is chromatographed on silica using a DCM/MeOH mixture (99.4/0.6; v/v) as the eluent. The expected product crystallizes from iso ether. m=0.160 g. M.p.=164° C.

EXAMPLE 21

5-Chloro-1-[4-(N',N'-diethylureido)-2-methoxybenzyl]-1,3-dihydro-3-spirocyclohexaneindol-2-one 1.64 ml of diethylamine are added to a solution of 295 mg of the compound prepared in Example 17 in 20 ml of EtOH and 5.5 ml of DCM and the mixture is stirred for 24 hours at RT. The solvents are evaporated off under vacuum and the residue is chromatographed on silica using a DCM/MeOH mixture (99/1; v/v) as the eluent. The expected product is taken up with heptane and filtered off. m=0.235 g. M.p.= 108° C.

The compounds according to the invention described in Table 3 below were prepared using the procedures described above.

TABLE 3

| N° Ex. | R₁ | CR₃R₄ | R₅ | R₆ | M.p. °C. or NMR |
|---|---|---|---|---|---|
| 22 (a) | H | cyclohexane | 3-MeO— | MeO— | 106 |
| 23 (b) | H | 4-piperidine | 2-MeO— | MeO— | NMR |
| 24 (c) | Cl— | cyclohexane | H— | MeO— | 80 |
| 25 (d) | Cl— | cyclohexane | 2-MeO— | MeO— | 106 |
| 26 (d) | Cl— | 4,4-dimethylcyclohexane | 2-MeO— | MeO— | 141 |
| 27 (a) | Cl— | cyclohexane | 3-MeO— | MeO— | 117 |
| 28 (d) | MeO— | cyclohexane | 2-MeO— | MeO— | 124 |
| 29 (a) | MeO— | cyclohexane | 3-MeO— | MeO— | 110 |
| 30 (a) | EtO— | cyclohexane | 3-MeO— | MeO— | 88 |
| 31 (e) | EtO— | cyclohexane | 2-MeO— | tBuNHCO— | 187 |
| 32 (f) | Cl— | cyclohexane | H— | F₃C— | 90 |
| 33 (g) | H— | cyclohexane | H— | O₂N— | 118 |
| 34 (g) | Cl— | cyclohexane | H— | O₂N— | 139 |
| 35 (h) | Cl— | cyclohexane | 2-Me— | O₂N— | 144 |
| 36 (i) | Cl— | cyclohexane | 3-MeO— | O₂N— | 80 |
| 37 (g) | MeO— | cyclohexane | H— | O₂N— | 106 |
| 38 (h) | MeO— | cyclohexane | 2-Me— | O₂N— | 133 |
| 39 (j) | MeO— | cyclohexane | 2-MeO— | O₂N— | 200 |
| 40 (j) | EtO— | 4,4-dimethylcyclohexane | 2-MeO— | O₂N— | 106 |
| 41 (k) | Cl— | cyclohexane | H— | H₂N— | 136 |
| 42 (k) | Cl— | cyclohexane | 2-Me— | H₂N— | 157 |
| 43 (k) | Cl— | cyclohexane | 3-MeO— | H₂N— | 113 |
| 44 (k) | MeO— | cyclohexane | H— | H₂N— | 192 |
| 45 (k) | MeO— | cyclohexane | MeO— | H₂N— | 165 |
| 46 (l) | Cl— | cyclohexane | 2-MeO— | MeCONH— | 194 |
| 47 (l) | Cl— | cyclohexane | 2-MeO— | C₆H₁₁CONH— | 143 |
| 48 (l) | Cl— | cyclohexane | 2-MeO— | 2-Me-C₆H₄-CONH— | 190 |
| 49 (l) | Cl— | cyclohexane | 2-MeO— | 4-pyridyl-CONH— | 205 |
| 50 (l) | MeO— | cyclohexane | 2-MeO— | MeCONH— | 202 |
| 51 (l) | MeO— | cyclohexane | H— | 2-Me-C₆H₄-CONH— | 167 |
| 52 (l) | MeO— | cyclohexane | 2-MeO— | 2-Me-C₆H₄-CONH— | 157 |
| 53 (m) | Cl— | cyclohexane | H— | PhOCONH— | 186 |
| 54 (m) | Cl— | cyclohexane | 3-MeO— | PhOCONH— | 112 |
| 55 (n) | Cl— | cyclohexane | H— | Et₂NCONH— | 190 |
| 56 (n) | Cl— | cyclohexane | 3-MeO— | Et₂NCONH— | 108 |
| 57 (o) | Cl— | cyclohexane | 2-Me— | MeNHCONH— | 153 |
| 58 (n) | EtO— | cyclohexane | 2-MeO— | Et₂NCONH— | 131 |

TABLE 3-continued

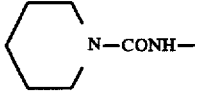

| N° Ex. | R₁ | CR₃R₄ | R₅ | R₆ | M.p. °C. or NMR |
|---|---|---|---|---|---|
| 59 (p) | EtO— | cyclohexane | 2-MeO— | ⟨N—CONH—⟩ (cyclohexyl) | 133 |
| 60 (d) | Cl— | N-methyl-4-piperidine | 2-MeO— | MeO— | 64 |
| 61 (m) | EtO— | cyclohexane | 2-MeO— | PhOCONH— | 170 |
| 62 (j) | EtO— | (tricyclic) | 2-MeO— | O₂N— | 88 |
| 63 (q) | EtO— | (tricyclic) | 2-MeO— | H₂N— | 96 |
| 64 (r) | EtO— | (tricyclic) | 2-MeO— | Et₂NCONH— | 126 |
| 65 (j) | EtO— | 4-tetrahydropyrane | 2-MeO— | O₂N— | 163 |
| 66 (s) | EtO— | 4-tetrahydropyrane | 2-MeO— | H₂N— | 171 |
| 67 (r) | EtO— | 4-tetrahydropyrane | 2-MeO— | Et₂NCONH— | 98 |
| 68 (1) (j) | EtO— | 4-methoxycyclohexane | 2-MeO— | O₂N— | oil |
| 69 (1) (s) | EtO— | 4-methoxycyclohexane | 2-MeO— | H₂N— | 92 |
| 70 (1) (r) | EtO— | 4-methoxycyclohexane | 2-MeO— | Et₂NCONH— | 62 |

NMR spectrum for Example 23 at 200 MHz in DMSO:
1.6–1.9 ppm: m: 4H
2.9–3.3 ppm: m: 4H
3.8 ppm: s: 3H
3.9 ppm: s: 3H
4.8 ppm: s: 2H
6.5 ppm: d of d: 1H
6.65 ppm: d: 1H
6.85 ppm: d: 1H
6.95 ppm: d: 1H
7.1 ppm: t: 1H
7.25 ppm: t: 1H
7.6 ppm: d: 1H (a) This compound is prepared by the procedure described in EXAMPLE 1.

(b) This compound is prepared by the following procedure: A mixture of 0.79 g of the compound obtained in EXAMPLE 3 and 1.4 g of KOH in 5 ml of 95° EtOH is refluxed for 4 hours. After cooling, water is added, the mixture is extracted with ether, the organic phase is extracted with a 3N solution of HCl, the acidic aqueous phase is rendered basic by the addition of a 10% solution of NaOH, extracted with ether, washed with water and dried over sodium sulfate and the solvent is evaporated off under vacuum. The residue is chromatographed on silica using a DCM/MeOH mixture (80/20; v/v, then 50/50; v/v) as the eluent to give 0.31 g of the expected product.

(c) This compound is prepared by the procedure described in EXAMPLE 1 using 1-chloromethyl-4-methoxybenzene.

(d) This compound is prepared by the procedure described in EXAMPLE 2.

(e) This compound is prepared by the following procedure: A mixture of 0.6 g of the compound obtained in EXAMPLE 6, 1 ml of tert-butylamine, 0.73 g of BOP, 2 ml of DIPEA and 45 ml of DCM is stirred for 1 hour at RT. It is washed with a 1N solution of HCl, with water, with a saturated solution of NaHCO₃ and with water and dried over Na₂SO₄ and the solvent is evaporated off under vacuum. The residue is chromatographed on silica using a DCM/MeOH mixture (98/2; v/v) as the eluent to give 0.295 g of the expected product after crystallization from iso ether.

(f) This compound is prepared by the procedure described in EXAMPLE 1 starting from 1-bromomethyl-4-trifluoromethylbenzene.

(g) This compound is prepared by the procedure described in EXAMPLE 8 starting from 1-bromomethyl-4-nitrobenzene.

(h) This compound is prepared by the procedure described in EXAMPLE 8 starting from 1-bromomethyl-2-methyl-4-nitrobenzene.

(i) This compound is prepared by the procedure described in EXAMPLE 8 starting from 1-bromomethyl-3-methoxy-4-nitrobenzene.

(j) This compound is prepared by the procedure described in EXAMPLE 8.

(k) This compound is prepared by the procedure described in EXAMPLE 9 starting from the corresponding nitro compound.

(l) This compound is prepared by the procedure described in EXAMPLE 12 starting from the corresponding amino compound and using the appropriate acid chlorides.

(m) This compound is prepared by the procedure described in EXAMPLE 17 starting from the corresponding amino compound.

(n) This compound is prepared by the procedure described in EXAMPLE 21 starting from the corresponding phenoxycarbonylamino compound.

(o) This compound is prepared by the procedure described in EXAMPLE 18 starting from the corresponding amino compound.

(p) This compound is prepared by the procedure described in EXAMPLE 21 starting from the corresponding phenoxycarbonylamino compound and using piperidine.

(q) This compound is prepared by the following procedure: A mixture of 1.26 g of the compound of EXAMPLE 62 and 1.37 g of tin powder in 15 ml of EtOH is cooled to 10° C., 2.73 ml of concentrated HCl are added and the mixture is then heated at 40° C. for 1 hour. After cooling, a saturated solution of $NaHCO_3$ is added, the mixture is extracted with AcOEt and dried over $Na_2SO_4$ and the solvent is evaporated off under vacuum. The residue is chromatographed on silica using DCM as the eluent to give 0.93 g of the expected product.

(r) This compound is prepared by the procedures described in EXAMPLE 17 and then in EXAMPLE 21.

(s) This compound is prepared by the procedure described in note (q) above.

(1) This compound is prepared from the compound obtained in Preparation 14 (isomer B: the more polar compound).

(2) This compound is prepared from the compound of EXAMPLE 68.

(3) This compound is prepared from the compound of EXAMPLE 69.

What is claimed is:

1. A compound of the formula:

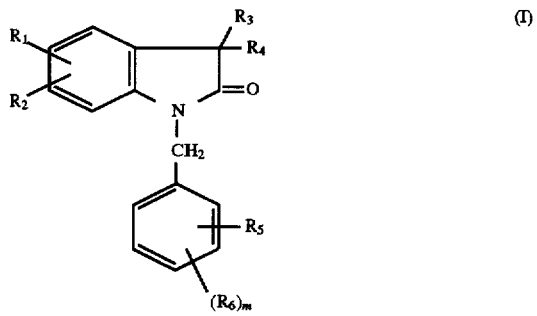

in which:

$R_1$ and $R_2$ are each independently a hydrogen; a halogen; a hydroxyl; an ω-halogeno($C_1$–$C_7$)alkoxy; a ($C_1$–$C_7$) alkyl; a trifluoromethyl; a ($C_1$–$C_7$)alkoxy; a polyhalogeno($C_1$–$C_7$)alkoxy; an ω-hydroxy($C_2$–$C_7$) alkoxy; an ω-methoxy($C_2$–$C_7$)alkoxy; an ω-amino ($C_2$–$C_7$)alkoxy which is free or substituted by one or two ($C_1$–$C_7$)alkyls; a ($C_3$–$C_7$)cycloalkoxy; a ($C_3$–$C_7$) cycloalkylmethoxy; a phenoxy; a benzyloxy; a ($C_1$–$C_7$) alkylthio; a phenylthio; a nitro; an amino which is free or substituted by one or two ($C_1$–$C_7$)alkyls; a cyano; a formyl; a ($C_1$–$C_7$)alkylcarbonyl; a benzoyl; a formyloxy; a ($C_1$–$C_7$)alkylcarbonyloxy; a benzoyloxy; a ($C_1$–$C_7$)alkylsulfonamido; a phenylsulfonamido; a benzylsulfonamido; a ($C_1$–$C_7$)alkylcarbonyl-amino; a ($C_1$–$C_7$)alkoxycarbonylamino; a ureido which is unsubstituted or substituted by a phenyl, a benzyl or one or two ($C_1$–$C_7$)alkyls; or a thioureido which is unsubstituted or substituted by a phenyl, a benzyl or one or two ($C_1$–$C_7$)alkyls, with the proviso that $R_1$ and $R_2$ are not simultaneously hydrogen;

$R_3$ and $R_4$ together form a group —$(CH_2)_p X(CH_2)_q$—; or $R_3$ and $R_4$, together with the carbon to which they are bonded, form an optionally fused, saturated or unsaturated $C_3$–$C_{12}$ hydrocarbon ring which is unsubstituted or substituted by one or more ($C_1$–$C_7$)alkyl groups, by a ($C_3$–$C_5$)spirocycloalkyl, by an oxo group or by one or two hydroxyl groups, said hydroxyl group(s) being unsubstituted or substituted by a group selected from the group consisting of a ($C_1$–$C_4$)alkyl, a ($C_1$–$C_2$) alkoxy($C_1$–$C_4$)alkyl, a phenyl($C_1$–$C_2$)alkoxy($C_1$–$C_4$) alkyl, a tetra-hydrofuranyl and a tetrahydropyranyl;

$R_5$ is hydrogen or has one of the meanings designated for $R_6$;

$R_6$ is a halogen; a ($C_1$–$C_7$)alkyl; a trifluoromethyl; a cyano; a nitro; a hydroxylamino; a hydroxyl; a carboxyl; a guanidino which is unsubstituted or substituted in the 1-position by a ($C_1$–$C_7$)alkyl and/or in the 3-position by one or two ($C_1$–$C_7$)alkyls, a phenyl or a benzyl and/or in the 2-position by a cyano; a group —$OR_7$; a group —$SR_7$; a formyl; a ($C_1$–$C_7$) alkylcarbonyl; a benzoyl; a ($C_1$–$C_7$)alkoxycarbonyl; a phenoxycarbonyl; a benzyloxycarbonyl; a group —$CONR_{17}R_{18}$; a group —$CSNR_{11}R_{19}$; a group —$SO_2NR_{20}R_{21}$; a ($C_1$–$C_7$)alkyl-sulfonamido; a group —$NHSO_2$—Ar; a benzylsulfonamido; an aminosulfonamido in which the amino is free or substituted by $R_{16}$ and $R_{22}$; a group —$NR_8R_9$; a group —CO—NH—$CR_{10}R_{23}$—$COR_{12}$; or a group —$CH_2NR_8R_9$;

$R_7$ is a ($C_1$–$C_7$)alkyl; a phenyl; a benzyl; a ($C_3$–$C_7$) cycloalkyl; a ($C_2$–$C_7$)alkenyl; an ω-halogeno($C_2$–$C_7$) alkyl; a polyhalogeno($C_1$–$C_7$)alkyl; an ω-hydroxy $(C_2-C_7)$alkyl; a formyl; a $(C_1-C_7)$alkylcarbonyl; a benzoyl; an ω-carboxy$(C_1-C_7)$alkyl; an ω-$(C_1-C_7)$ alkoxycarbonyl$(C_1-C_7)$alkyl; an ω-benzyloxycarbonyl $(C_1-C_7)$alkyl; an ω-amino$(C_2-C_7)$alkyl in which the amino group is free or substituted by one or two $(C_1-C_7)$alkyls, or in the form of an ammonium ion; or an ω-carbamoyl$(C_1-C_7)$alkyl in which the carbamoyl is free or substituted by one or two $(C_1-C_7)$alkyls;

$R_8$ and $R_9$ are each independently a hydrogen; a $(C_1-C_7)$ alkyl; or a group —$CH_2$—Ar; $R_9$ can also be a group Ar; a $(C_3-C_8)$alkenyl; a formyl; a $(C_1-C_7)$ alkylcarbonyl; a $(C_1-C_7)$alkylthiocarbonyl; a $(C_3-C_7)$ cycloalkylcarbonyl; a $(C_3-C_7)$cycloalkylthiocarbonyl; an ω-amino$(C_2-C_7)$alkylcarbonyl in which the amino is free or substituted by one or two $(C_1-C_7)$alkyls; an ω-hydroxy$(C_1-C_7)$alkylcarbonyl; an ω-benzyloxy $(C_1-C_7)$alkylcarbonyl; a pyridylcarbonyl; a methylpyridylcarbonyl; a thienylcarbonyl; a group —CO—Ar; a group —CO—$CH_2$—Ar; a $(C_1-C_7)$alkoxycarbonyl; a phenoxycarbonyl; a phenoxythiocarbonyl; a benzyloxy-carbonyl; a group —CO—$CR_{10}R_{23}$—$NR_{11}R_{19}$; a group —$CR_{10}R_{23}COR_{12}$; a group —$(CH_2)_t$ $COR_{12}$; a group —$CO(CH_2)_uCOR_{12}$; a group —$CONR_{14}R_{24}$; a group —$CSNR_{14}R_{24}$; or a heterocyclic radical selected from pyrazolyl, imidazolyl, triazolyl, tetrazolyl, pyridyl, pyridazinyl, pyrimidinyl and thiazolyl; —or else $R_8$ and $R_9$, together with the nitrogen atom to which they are bonded, form hydantoin; N-methylhydantoin; or a heterocyclic radical selected from pyrrol-1-yl, Δ,3-pyrrolin-1-yl, pyrrolidin-1-yl and isoindolin-2-yl in which the benzene ring is unsubstituted or substituted by a halogen, a $(C_1-C_7)$alkyl, a trifluoromethyl or a methoxy;

$R_{10}$ and $R_{23}$ are each independently hydrogen; a $(C_1-C_7)$ alkyl; or a benzyl;

or $R_{10}$ and $R_{23}$, together with the carbon atom to which they are bonded, form a $(C_3-C_7)$cycloalkyl;

$R_{11}$ and $R_{19}$ are each independently hydrogen; or a $(C_1-C_7)$alkyl;

$R_{12}$ is a hydroxyl; a $(C_1-C_7)$alkoxy; or an amino which is free or substituted by one or two $(C_1-C_7)$alkyls;

$R_{13}$ is hydrogen; a $(C_1-C_7)$alkyl; a phenyl; a benzyl; a formyl; a $(C_1-C_7)$alkylcarbonyl; a benzoyl; a $(C_1-C_7)$ alkoxycarbonyl; or a carbamoyl which is unsubstituted or substituted by one or two $(C_1-C_7)$alkyls;

$R_{14}$ and $R_{24}$ are each independently hydrogen; or a $(C_1-C_7)$alkyl; $R_{24}$ can also be a $(C_1-C_7)$alkyl substituted by $R_{15}$; a group Ar; a $(C_3-C_7)$cycloalkyl; or an adamantyl;

or $R_{14}$ and $R_{24}$, together with the nitrogen atom to which they are bonded, form a heterocycle selected from morpholine, thiomorpholine, piperazine, azetidine, pyrrolidine, piperidine and perhydroazepine, said heterocycle being unsubstituted or substituted by one or more methyl groups, a phenyl or an amino group which is free or carries a protecting group;

$R_{15}$ is a group Ar; a pyridyl; a hydroxyl; a $(C_1-C_7)$alkoxy; a group —$NR_{11}R_{19}$; a carboxyl; or a $(C_1-C_7)$ alkoxycarbonyl;

$R_{16}$ and $R_{22}$ are each independently a hydrogen; or a $(C_1-C_7)$alkyl;

or $R_{16}$ and $R_{22}$, together with the nitrogen atom to which they are bonded, form a heterocycle selected from azetidine, pyrrolidine, piperidine, piperazine and perhydroazepine, said heterocycle being unsubstituted or substituted by one or more methyl groups;

$R_{17}$ and $R_{18}$ are each independently hydrogen; or a $(C_1-C_8)$alkyl; $R_{18}$ can also be a $(C_3-C_7)$cycloalkyl which is unsubstituted or substituted by a $(C_1-C_4)$ alkyl; a group Ar; a pyridyl; a methylpyridyl; a piperid-4-yl substituted in the 1-position by $R_{27}$; a piperid-1-yl; a pyrrolidin-1-yl; a morpholin-4-yl; or a $(C_1-C_7)$alkyl substituted by one or more halogens or by $R_{26}$;

or else $R_{17}$ and $R_{18}$, together with the nitrogen atom to which they are bonded, form a heterocyclic radical $R_{25}$;

$R_{20}$ and $R_{21}$ are each independently hydrogen; or a $(C_1-C_7)$alkyl;

or else $R_{20}$ and $R_{21}$, together with the nitrogen atom to which they are bonded, form a heterocyclic radical $R_{25}$;

$R_{25}$ is a morpholin-4-yl; a thiomorpholin-4-yl; an azetidin-1-yl which is unsubstituted or substituted in the 3-position by a group —$NR_{11}R_{19}$, a $(C_1-C_7)$alkyl, a phenyl, a benzyl, or a $(C_1-C_7)$alkylcarbonyl; a perhydroazepin-1-yl; a piperazin-1-yl which is unsubstituted or substituted in the 4-position by a $(C_1-C_7)$ alkyl, a phenyl, a benzyl, a $(C_1-C_7)$alkylcarbonyl, a $(C_1-C_7)$alkoxycarbonyl or a benzyloxycarbonyl; a piperid-1-yl which is unsubstituted or substituted in the 4-position by a $(C_1-C_7)$alkyl, a phenyl, a benzyl, a $(C_1-C_7)$alkylcarbonyl or a group —$NR_{11}R_{19}$; or a pyrrolidin-1-yl which is unsubstituted or substituted by a $(C_1-C_7)$alkyl, a phenyl, a benzyl, a $(C_1-C_7)$ alkylcarbonyl, a hydroxymethyl, a carboxyl, a $(C_1-C_7)$ alkoxycarbonyl or a carbamoyl which is unsubstituted or substituted by one or two $(C_1-C_7)$alkyls;

$R_{26}$ is a hydroxyl; a $(C_1-C_7)$alkoxy; a cyano; a carboxyl; a $(C_1-C_7)$alkoxycarbonyl; a benzyloxycarbonyl; a group —$NR_{11}R_{19}$; a carbamoyl which is free or substituted by one or two $(C_1-C_7)$alkyls; a pyrrolidin-1-ylcarbonyl; a piperid-1-ylcarbonyl; a perhydroazepin-1-ylcarbonyl; a group Ar; a $(C_3-C_7)$cycloalkyl; an adamantyl; or a heterocyclic radical selected from a pyridyl, a methylpyridyl, a furanyl, a tetrahydrofuranyl, a thienyl, a methylthienyl, a pyrrolidin-1-yl, a piperid-1-yl and a perhydroazepin-1-yl;

$R_{27}$ is a hydrogen; a $(C_1-C_7)$alkyl; a phenyl; a benzyl; a formyl; a $(C_1-C_7)$alkylcarbonyl; a benzoyl; a $(C_1-C_7)$ alkoxycarbonyl; a phenoxycarbonyl; or a carbamoyl which is free or substituted by one or two $(C_1-C_7)$ alkyls;

Ar is a phenyl which is unsubstituted or monosubstituted or polysubstituted by a substituent selected from a halogen atom, a $(C_1-C_7)$alkyl, a trifluoromethyl, a hydroxyl, a $(C_1-C_7)$alkoxy, a carboxyl, a $(C_1-C_7)$ alkoxycarbonyl, a $(C_1-C_7)$alkylcarbonyloxy, a nitro, a cyano, an amino, a $(C_1-C_7)$alkylamino and a $(C_1-C_7)$ dialkylamino, said substituents being identical or different;

m is 1, 2, 3 or 4, provided that when m is 2, 3 or 4 each $R_6$ independently represents a halogen, a $(C_1-C_7)$alkyl or a $(C_1-C_7)$alkoxy;

p and q are each an integer, it being possible for their sum to vary from 3 to 6;

t is an integer which can vary from 2 to 5;

u is an integer which can vary from 0 to 3;

X is oxygen, a group —$NR_{13}$, a group —$N(O)R_{13}$ or a group $S(O)_x$; and x is 0, 1 or 2;

provided that at least one of —$CR_3R_4$, $R_5$ and $R_6$ contains one or more heterocyclic radicals;

and its salts.

2. A compound according to claim 1 wherein $R_1$ is in the 5-position of the 1,3-dihydroindol-2-one and $R_2$ is hydrogen.

3. A compound according to claim 1 wherein $R_1$ is a chlorine or fluorine atom or an ethoxy group in the 5-position of the 1,3-dihydroindol-2-one and $R_2$ is hydrogen.

4. A compound according to claim 1 wherein $R_3$ and $R_4$, together with the carbon to which they are bonded, form a $C_3$–$C_{12}$ hydrocarbon ring.

5. A compound according to claim 1 wherein $R_3$ and $R_4$, together with the carbon to which they are bonded, form a cycloheptane, an adamantane, a tricyclo[5.2.1.0$^{2,6}$]decane, a tricyclo[5.2.1.0$^{2,6}$]dec-8-ene, a bicyclo[2.2.1]heptane, a bicyclo[3.3.1]nonane or a cyclohexane which is unsubstituted or substituted by a $C_3$–$C_5$-spirocycloalkyl, by one or two $C_1$–$C_7$-alkyls or by a $C_1$–$C_4$-alkoxy.

6. A compound according to claim 1 wherein $R_5$ is either hydrogen or a methoxy group in the 2-position and $R_6$ in the 4-position is a group selected from:
 a methoxy;
 a ($C_1$–$C_7$)alkylcarboxamido;
 a group —NHCO—Ar;
 a group —CONR$_{17}$R$_{18}$; and
 a group —NR$_8$CONR$_{14}$R$_{24}$,
in which Ar, $R_{17}$, $R_{18}$, $R_8$, $R_{14}$ and $R_{24}$ are as defined for (I) in claim 1.

7. A pharmaceutical composition containing (i) an effective amount of a compound according to claim 1 or a pharmaceutically acceptable salt thereof and (ii) suitable excipients.

8. A compound according to claim 1 of formula (I), in which:

$R_1$ and $R_2$ are each independently a hydrogen; a halogen; a hydroxyl; an halogeno($C_1$–$C_7$)alkoxy; a ($C_1$–$C_7$) alkyl; a trifluoromethyl; a ($C_1$–$C_7$)alkoxy; a polyhalogeno($C_1$–$C_7$)alkoxy; an ω-hydroxy($C_2$–$C_7$) alkoxy; an ω-methoxy($C_2$–$C_7$)alkoxy; or an ω-amino ($C_2$–$C_7$)alkoxy which is free or substituted by one or two ($C_1$–$C_7$)alkyls; a ($C_3$–$C_7$)cycloalkoxy; a ($C_3$–$C_7$) cycloalkylmethoxy; with the proviso that $R_1$ and $R_2$ are not simultaneously hydrogen;

$R_3$ and $R_4$ together form a group —(CH$_2$)$_p$X(CH$_2$)$_q$—; or $R_3$ and $R_4$, together with the carbon to which they are bonded, form an optionally fused, saturated or unsaturated $C_3$–$C_{12}$ hydrocarbon ring which is unsubstituted or substituted by one or more ($C_1$–$C_7$)alkyl groups, by a ($C_3$–$C_5$)spirocycloalkyl, by an oxo group or by one or two hydroxyl groups, said hydroxyl group(s) being unsubstituted or substituted by a group selected from the group consisting of a ($C_1$–$C_4$)alkyl, a ($C_1$–$C_2$) alkoxy($C_1$–$C_4$)alkyl, a phenyl($C_1$–$C_2$)alkoxy($C_1$–$C_4$) alkyl, a tetrahydrofuranyl and a tetrahydropyranyl;

$R_5$ is hydrogen or a group —OR$_7$;

$R_6$ is a halogen; a nitro; a group —OR$_7$; a group —SR$_7$; a group —NR$_8$R$_9$; a group —CONR$_{17}$R$_{18}$ or a group —CH$_2$NR$_8$R$_9$;

$R_7$ is a ($C_1$–$C_7$)alkyl; a ($C_3$–$C_7$)cycloalkyl; an ω-halogeno ($C_2$–$C_7$)alkyl; a polyhalogeno($C_1$–$C_7$)alkyl; an ω-hydroxy($C_2$–$C_7$)alkyl; an ω-carboxy($C_1$–$C_7$)alkyl; an ω-amino($C_2$–$C_7$)alkyl in which the amino group is free or substituted by one or two ($C_1$–$C_7$)alkyls;

$R_8$ is hydrogen or a ($C_1$–$C_7$)alkyl;

$R_9$ is hydrogen, a ($C_1$–$C_7$)alkyl; a ($C_1$–$C_7$)alkylcarbonyl; a group COAr; a pyridylcarbonyl; a group —CONR$_{14}$R$_{24}$; or a group —CSNR$_{14}$R$_{24}$;

or else $R_8$ and $R_9$, together with the nitrogen atom to which they are bonded, form a Δ3-pyrrolin-1-yl;

$R_{11}$ and $R_{19}$ are each independently hydrogen; or a ($C_1$–$C_7$)alkyl;

$R_{13}$ is hydrogen; a ($C_1$–$C_7$)alkyl; a formyl; a ($C_1$–$C_7$) alkylcarbonyl; a ($C_1$–$C_7$)alkoxycarbonyl;

$R_{14}$ is hydrogen or a ($C_1$–$C_7$)alkyl;

$R_{24}$ is hydrogen; a ($C_1$–$C_7$)alkyl; a ($C_1$–$C_7$)alkyl substituted by $R_{15}$; or a ($C_3$–$C_7$)cycloalkyl;

or $R_{14}$ and $R_{24}$, together with the nitrogen atom to which they are bonded, form a piperidine;

$R_{15}$ is a group Ar; a pyridyl; a hydroxyl; a ($C_1$–$C_7$)alkoxy; a group —NR$_{11}$R$_{19}$; a carboxyl; or a ($C_1$-$C_7$) alkoxycarbonyl;

$R_{17}$ is hydrogen or a ($C_1$–$C_7$)alkyl;

$R_{18}$ is hydrogen; a ($C_1$–$C_8$)alkyl; a ($C_3$–$C_7$)cycloalkyl which is unsubstituted or substituted by a ($C_1$–$C_4$) alkyl;

or else $R_{17}$ and $R_{18}$, together with the nitrogen atom to which they are bonded, form a heterocyclic radical selected from the group consisting of morpholin-4-yl, thiomorpholin-4-yl, azetidin-1-yl, piperazin-1-yl, piperid-1-yl and pyrrolidin-1-yl;

Ar is a phenyl which is unsubstituted or monosubstituted or polysubstituted by a substituent selected from a halogen atom, a ($C_1$–$C_7$)alkyl, a trifluoromethyl, a hydroxyl, a ($C_1$–$C_7$)alkoxy, a carboxyl, a ($C_1$–$C_7$) alkoxycarbonyl, a ($C_1$–$C_7$)alkylcarbonyloxy, a nitro, a cyano, an amino, a ($C_1$–$C_7$)alkylamino and a ($C_1$–$C_7$) dialkylamino, said substituents being identical or different;

m is 1, 2, 3 or 4, provided that when m is 2, 3 or 4 ech $R_6$ independently represents a halogen, a ($C_1$–$C_7$)alkyl or a ($C_1$–$C_7$)alkoxy;

p and q are each an integer, it being possible for their sum to vary from 3 to 6;

X is oxygen or a group —NR$_{13}$;
provided that at least one of —CR$_3$R$_4$, $R_5$ and $R_6$ contains one or more heterocyclic radicals;
and its salts.

9. A compound according to claim 1 of formula (I), in which $R_3$ and $R_4$, together with the carbon to which they are bonded, form a piperidin-4 ring which is unsubstituted or substituted on the nitrogen by a ($C_1$–$C_7$)alkyl; and its salts.

10. A pharmaceutical composition containing (i) an effective amount of a compound according to claim 1 or a pharmaceutically acceptable salt thereof, (ii) an effective amount of another active principle selected from the group consisting of a converting enzyme inhibitor, an angiotensin II antagonist, a renin inhibitor, a peripheral vasodilator, a calcium inhibitor, a beta-blocker, an alpha-1-blocker and a diuretic and (iii) suitable excipients.

11. A pharmaceutical composition containing (i) effective amounts of two compound according to claim 1 or pharmaceutically acceptable salts thereof, one being a specific $V_1$ receptor antagonist and the other being a specific V2 receptor antagonist and (ii) suitable excipients.

12. A pharmaceutical composition containing (i) effective amounts of two compound according to claim 1 or pharmaceutically acceptable salts thereof, one being a specific $V_1$ receptor antagonist and the other being a specific oxytocin antagonist and (ii) suitable excipients.

* * * * *